United States Patent
Kurosaki et al.

(10) Patent No.: US 10,328,245 B2
(45) Date of Patent: *Jun. 25, 2019

(54) POSITIONING METHOD FOR BALLOON COATING

(71) Applicant: TERUMO KABUSHIKI KAISHA, Shibuya-ku, Tokyo (JP)

(72) Inventors: Yasuo Kurosaki, Kanagawa (JP); Ryosuke Suzuki, Kanagawa (JP); Eisuke Furuichi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/937,429

(22) Filed: Mar. 27, 2018

(65) Prior Publication Data

US 2018/0214676 A1 Aug. 2, 2018

Related U.S. Application Data

(63) Continuation of application No. 15/282,563, filed on Sep. 30, 2016, now Pat. No. 9,937,328, which is a
(Continued)

(30) Foreign Application Priority Data

Apr. 1, 2014 (JP) .................. 2014-075325

(51) Int. Cl.
*A61M 25/10* (2013.01)
*B05C 5/02* (2006.01)
(Continued)

(52) U.S. Cl.
CPC ............. *A61M 25/10* (2013.01); *A61L 29/08* (2013.01); *A61L 29/16* (2013.01);
(Continued)

(58) Field of Classification Search
None
See application file for complete search history.

(56) References Cited

U.S. PATENT DOCUMENTS

| 6,558,405 B1 | 5/2003 | McInnes |
| 8,597,720 B2 | 12/2013 | Hoffmann et al. |

(Continued)

FOREIGN PATENT DOCUMENTS

| AU | 2014250424 B2 | 10/2014 |
| EP | 0128859 A1 | 12/1984 |

(Continued)

OTHER PUBLICATIONS

Office Action issued by the Australian Patent Office in corresponding Australian Patent Application No. 2014250424 dated Dec. 8, 2015 (3 pages).

(Continued)

*Primary Examiner* — Cachet I Sellman
(74) *Attorney, Agent, or Firm* — Buchanan Ingersoll & Rooney PC

(57) ABSTRACT

A method is disclosed for forming a coating layer on an outer surface of a balloon of a balloon catheter. The method includes supplying a coating solution containing a drug and a solvent through an end portion of a flexible dispensing tube with an opening portion for discharging the coating solution through the end portion of the flexible dispensing tube; keeping in contact an opening portion-formed end portion side of the dispensing tube with the outer surface of the balloon in such a manner as to be oriented in a direction opposite to a rotating direction of the balloon; rotating the balloon about an axis of the balloon; and discharging the coating solution through the opening portion and applying the coating solution to the outer surface of the balloon while (Continued)

the dispensing tube is moved relative to the balloon in an axial direction of the balloon.

20 Claims, 20 Drawing Sheets

Related U.S. Application Data continuation of application No. PCT/JP2015/058548, filed on Mar. 20, 2015.

(51) Int. Cl.
    *B05C 13/02*      (2006.01)
    *A61L 29/08*      (2006.01)
    *A61L 29/16*      (2006.01)
    *B05B 13/04*      (2006.01)

(52) U.S. Cl.
    CPC ....... *A61M 25/1029* (2013.01); *B05C 5/0208* (2013.01); *B05C 13/025* (2013.01); *A61L 2300/416* (2013.01); *A61L 2420/02* (2013.01); *A61M 2025/105* (2013.01); *A61M 2025/1031* (2013.01); *A61M 2207/10* (2013.01); *B05B 13/0442* (2013.01)

(56) References Cited

U.S. PATENT DOCUMENTS

| | | | |
|---|---|---|---|
| 8,632,837 B2 * | 1/2014 | Gong | A61M 25/1027 118/300 |
| 2003/0144344 A1 | 7/2003 | Benigni et al. | |
| 2008/0097301 A1 | 4/2008 | Alpini et al. | |
| 2008/0097374 A1 | 4/2008 | Korleski et al. | |
| 2008/0118544 A1 | 5/2008 | Wang | |
| 2008/0226693 A1 | 9/2008 | Dave et al. | |
| 2008/0280026 A1 | 11/2008 | O'Conner et al. | |
| 2009/0093870 A1 | 4/2009 | Menendez et al. | |
| 2009/0246252 A1 | 10/2009 | Arps et al. | |
| 2009/0317537 A1 | 12/2009 | Andreacchi | |
| 2010/0034960 A1 | 2/2010 | Kindaichi et al. | |
| 2010/0040766 A1 | 2/2010 | Chappa et al. | |
| 2010/0049296 A1 | 2/2010 | Sarasam et al. | |
| 2010/0055294 A1 * | 3/2010 | Wang | B05D 1/002 427/2.25 |
| 2010/0104734 A1 | 4/2010 | Orosa et al. | |
| 2010/0179475 A1 * | 7/2010 | Hoffmann | A61L 29/16 604/103.02 |
| 2010/0209472 A1 | 8/2010 | Wang | |
| 2010/0272773 A1 | 10/2010 | Kangas et al. | |
| 2011/0015664 A1 | 1/2011 | Kangas et al. | |
| 2011/0022027 A1 | 1/2011 | Morishita et al. | |
| 2011/0281020 A1 | 11/2011 | Gong | |
| 2011/0295200 A1 | 12/2011 | Speck et al. | |
| 2012/0015019 A1 | 1/2012 | Pacetti et al. | |
| 2012/0100279 A1 | 4/2012 | Neumann et al. | |
| 2012/0128863 A1 | 5/2012 | Nguyen et al. | |
| 2012/0315376 A1 | 12/2012 | Nguyen et al. | |
| 2013/0142834 A1 | 6/2013 | Esfand et al. | |
| 2013/0337147 A1 * | 12/2013 | Chappa | A61M 25/1027 427/2.3 |
| 2014/0271775 A1 | 9/2014 | Cleek et al. | |
| 2014/0328998 A1 | 11/2014 | Chappa et al. | |
| 2014/0358122 A1 | 12/2014 | Yamashita et al. | |
| 2015/0328369 A1 | 11/2015 | Yamashita et al. | |
| 2015/0328371 A1 | 11/2015 | Yamashita et al. | |
| 2015/0328372 A1 | 11/2015 | Yamashita et al. | |
| 2016/0015861 A1 | 1/2016 | Yamashita et al. | |
| 2016/0310709 A1 | 10/2016 | Gotou et al. | |
| 2017/0014601 A1 | 1/2017 | Kurosaki et al. | |
| 2017/0014603 A1 | 1/2017 | Kurosaki et al. | |
| 2017/0014860 A1 | 1/2017 | Kurosaki et al. | |
| 2017/0021142 A1 | 1/2017 | Kurosaki et al. | |

FOREIGN PATENT DOCUMENTS

| | | |
|---|---|---|
| EP | 2944334 A1 | 11/2015 |
| JP | 59-207854 A | 11/1984 |
| JP | S59-207854 A | 11/1984 |
| JP | 2005-059225 A | 3/2005 |
| JP | 2010-509991 A | 4/2010 |
| JP | 2010-540159 A | 12/2010 |
| JP | 2012-514510 A | 6/2012 |
| JP | 2012-533338 A | 12/2012 |
| JP | 2013-514278 A | 4/2013 |
| WO | WO-2008/063576 A2 | 5/2008 |
| WO | WO-2008/063581 A2 | 5/2008 |
| WO | WO-2009/051614 A1 | 4/2009 |
| WO | WO-2009/051615 A1 | 4/2009 |
| WO | WO-2009/051616 A1 | 4/2009 |
| WO | WO-2009/051618 A1 | 4/2009 |
| WO | WO-2010/030995 A2 | 3/2010 |
| WO | WO-2010/079218 A1 | 7/2010 |
| WO | WO-2010/124098 A2 | 10/2010 |
| WO | WO-2011/008393 A2 | 1/2011 |
| WO | WO-2011/119159 A1 | 9/2011 |
| WO | WO-2013/181498 A1 | 12/2013 |
| WO | WO-2014/152360 A1 | 9/2014 |
| WO | WO-2014/163091 A1 | 10/2014 |

OTHER PUBLICATIONS

Buszman et al. "Tissue Uptake, Distribution, and Healing Response After Delivery of Paclitaxal via Second-Generation Iopromide-Based Balloon Coating", JACC; Cardiovascular Interventions, The American College of Cardiology Foundation, (Aug. 2013), vol. 6, No. 8, pp. 883-890.

Office Action issued by the Canadian Intellectual Property Office in corresponding Canadian Patent Application No. 2,908,420 dated Jan. 26, 2017 (4 pages).

Extended Search Report issued by the European Patent Ofgfice in corresponding European Patent Application No. 14779028.1 dated Jan. 25, 2017 (11 pages).

Extended Search Report issued by the European Patent Office in related European Patent Application No. 15709082.0 dated Mar. 8, 2017 (7 pages).

Extended Search Report issued by the European Patent Office in related European Patent Application No. 15709083.8 dated Mar. 8, 2017 (7 pages).

Extended Search Report issued by the European Patent Office in related European Patent Application No. 15709081.2 dated Mar. 8, 2017 (6 pages).

Gyoengyoesi et al. "TCT-807 Optical Coherence Tomography, Physiologic Vascular Function, Safety and Efficacy Preclinical Studies of Porcine Peripheral Vessels Dilated with Drug-Coated Balloon", (Oct. 29, 2013), JACC vol. 62/18/Suppl B, pp. B245.

International Search Report (PCT/ISA/210) dated Jun. 17, 2014, by the Japanese Patent Office as the International Searching Authority for International Application No. PCT/JP2014/059665.

International Search Report (PCT/ISA/210) dated Jun. 16, 2015, by the Japanese Patent Office as the International Searching Authority for International Application No. PCT/JP2015/058546.

Written Opinion (PCT/ISA/237) dated Jun. 16, 2015, by the Japanese Patent Office as the International Searching Authority for International Application No. PCT/JP2015/058546.

International Search Report (PCT/ISA/210) dated Jun. 16, 2015, by the Japanese Patent Office as the International Searching Authority for International Application No. PCT/JP2015/058547.

Written Opinion (PCT/ISA/237) dated Jun. 16, 2015, by the Japanese Patent Office as the International Searching Authority for International Application No. PCT/JP2015/058547.

Joner et al. "Comparative assessement of drug-eluting balloons in an advanced porcine model of coronary restenosis", Thrombosis and Haemostasis, (May 2011), vol. 105, No. 5, pp. 864-872.

Melder et al., "IN.PACT DEB Technology and Pre-clinical Science", Leipzig Interventional Course (LINC), 2013 (month unknown), pp. 1-18.

(56) References Cited

OTHER PUBLICATIONS

Poletto et al. "Characterization of Polyamide 66 Membranes Prepared by Phase Inversion using Formic Acid and Hydrochloric Acid Such as Solvents", May 5, 2011, 14(4), pp. 547-551.
Ranger™, "Paclitaxel-Coated PTA Balloon Catheter", Boston Scientific, retrieved on May 16, 2014, pp. 1-6.
Schmidt et al., "First Experience with Drug-Eluting Balloons in Infrapopliteal Arteries", Journal of the American College of Cardiology, (Sep. 2011), vol. 58, No. 11, pp. 1105-1109.
Virmani, "Pre-clinical safety data and technology review", Leipzig Interventional Course (LINC), CVPath Institute, Gaithersburg, Maryland, www.cvpath.org, 2014 (month unknown), pp. 1-22.
Virmani, "Pros and Cons of Different Technologies in Peripheral Arteries: Insights from a Pathologist", CVPath Institute Inc., Gaithersburg, Maryland, pp. 1-41.
Von Strandmann, "Effect of drug-coated balloon on porcine peripheral arteries: physiologic vascular function, safety and efficacy experiments", Euro PCR, 2013 (month unknown), pp. 1-20.
Yazdani et al., "Vascular, Downstream, and Pharmacokinetic Responses to Treatment with a Low Dose Drug-Coated Balloon in a Swine Femoral Artery Model", Catherization and Cardiovascular Interventions, Jan. 2014, vol. 83, No. 1, pp. 132-140.
Extended Search Report issued by the European Patent Office in related European Patent Application No. 15772370.1 dated Sep. 6, 2017 (7 pages).
Extended Search Report issued by the European Patent Office in related European Patent Application No. 15773037.5 dated Oct. 5, 2017 (7 pages).
International Search Report (PCT/ISA/210) issued by the Japanese Patent Office as the International Searching Authority for International Application No. PCT/JP2015/05848 dated Aug. 4, 2015.
Written Opinion (PCT/ISA/237) issued by the Japanese Patent Office as the International Searching Authority for International Application No. PCT/JP2015/058548 dated Aug. 4, 2015.
Office Action (Notification of Reasons for Refusal) dated Aug. 13, 2018, by the Japanese Patent Office in corresponding Japanese Patent Application No. 2016-511545 and an English Translation of the Office Action. (7 pages).

* cited by examiner

P1

×1000

P2

P4

× 1000

P5

P6

FIG.31
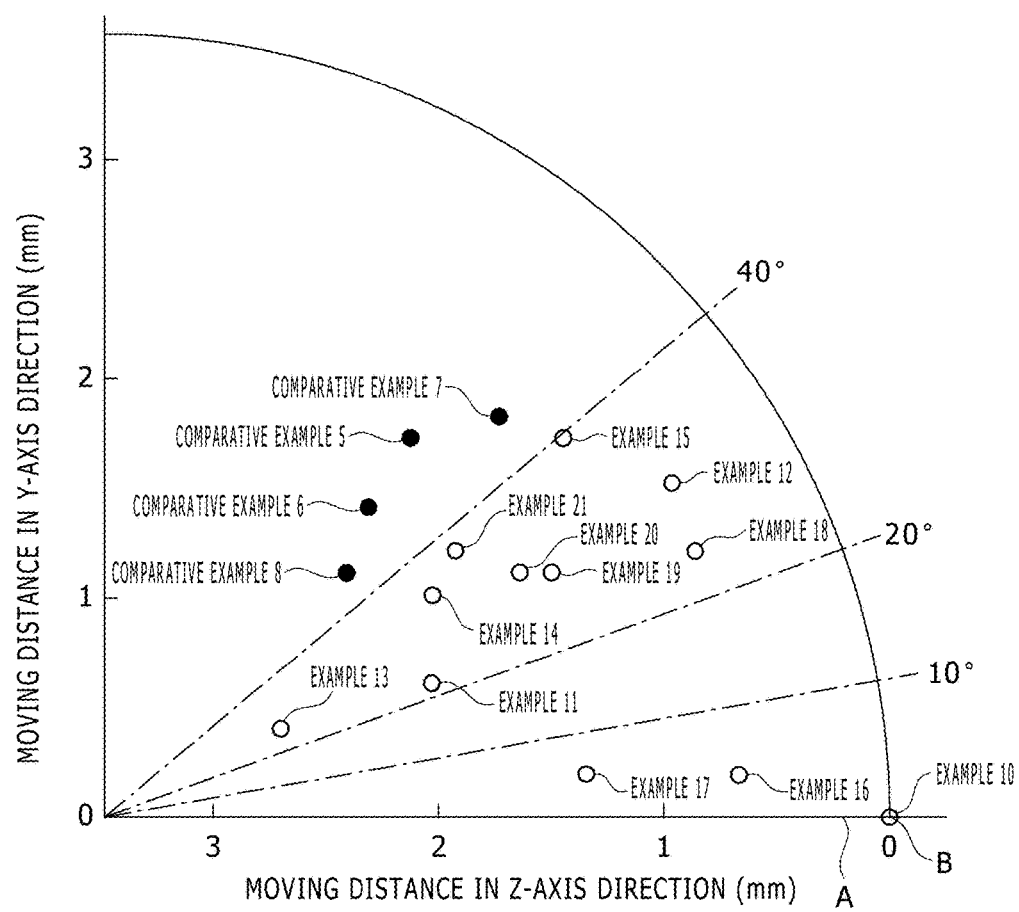
FIG. 32A    FIG. 32B    FIG. 32C
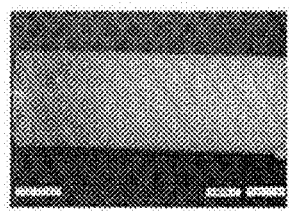 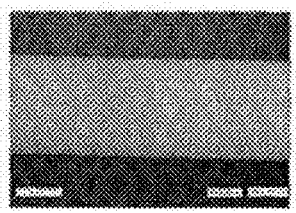 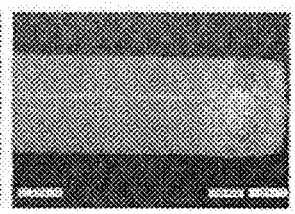

FIG. 33A  FIG. 33B  FIG. 33C
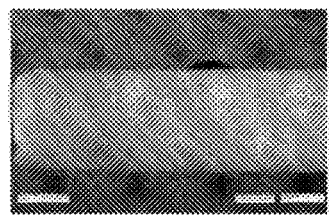 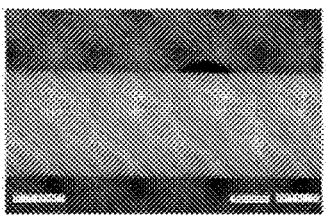 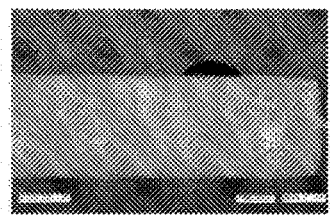
FIG. 34A  FIG. 34B  FIG. 34C
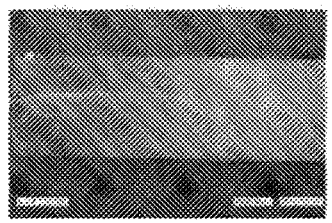 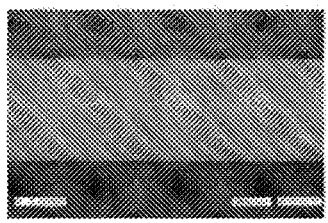 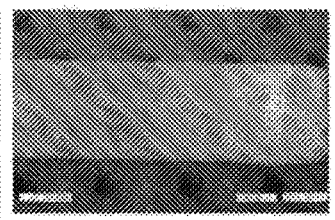
FIG. 35A  FIG. 35B  FIG. 35C
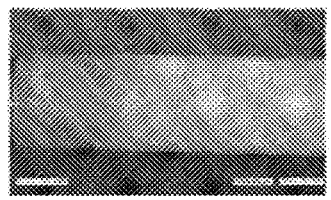 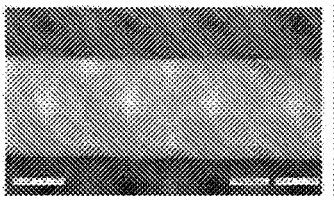 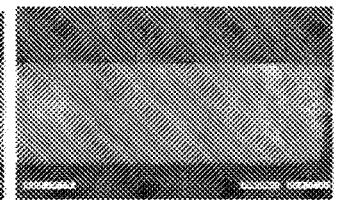

P7

POSITIONING METHOD FOR BALLOON COATING

CROSS-REFERENCES TO RELATED APPLICATIONS

This application is a continuation of U.S. patent application Ser. No. 15/282,563 filed on Sep. 30, 2016, which is a continuation of International Application No. PCT/JP2015/058548 filed on Mar. 20, 2015, which claims priority to Japanese Patent Application No. 2014-075325 filed on Apr. 1, 2014, the entire contents of each is incorporated herein by reference in their entirety.

TECHNICAL FIELD

The present disclosure generally relates to a positioning method for balloon coating for forming a coating layer containing a drug on a surface of a balloon.

BACKGROUND ART

In recent years, balloon catheters have been used for improving lesion affected areas (stenosed parts) generated in body lumens. A balloon catheter normally includes an elongated shaft portion, and a balloon, which is provided on the distal side of the shaft portion and is inflatable in the radial direction. After the balloon in a deflated state is brought to a target site in the body by way of a thin body lumen, the balloon is inflated, whereby the lesion affected area can be pushed wide open.

If a lesion affected area is forcibly pushed wide open, however, excessive proliferation of smooth muscle cells may occur, possibly causing new stenosis (restenosis) at the lesion affected area. In view of this, recently, drug eluting balloons (DEBs) wherein an outer surface of a balloon is coated with a drug for restraining stenosis have been used. The drug eluting balloon, by being inflated, is able to instantaneously release the drug contained in the coating on the outer surface of the drug eluting balloon to the lesion affected area and transfer the drug to the living body tissue, thereby restraining restenosis.

In recent years, it has been becoming clear that the morphological form of the drug in the coating on the balloon surface influences the releasing property of the drug from the balloon surface and/or the tissue transferability of the drug, at the lesion affected area. For this reason, it can be important to control the crystalline form or amorphous form of the drug.

A variety of methods have been proposed for coating a balloon with a drug. For example, U.S. Patent Application Publication No. 2010/055294 describes a method in which a coating liquid containing a drug is supplied to a surface of a balloon while the balloon is moved in its axial direction while being rotated and while the coating quantity is being controlled, and the coating liquid is dried to form a coating layer containing the drug.

SUMMARY OF INVENTION

The drug in the coating on the outer surface of the balloon can assume different morphological forms such as crystalline form, amorphous form, and mixed formed thereof, depending on various conditions such as the length of time of volatilization of the solvent. Neither of the crystalline form and the amorphous form is more desirable than the other, and it is desirable that the morphological form of the drug can be selected according to the purpose.

A balloon positioning method for balloon coating is disclosed by which the morphological form and the like of a drug in a coating formed on a balloon can be suitably set.

A positioning method is disclosed for balloon coating for forming a coating layer containing a water-insoluble drug on an outer surface of a balloon of a balloon catheter, the positioning method including a positioning step in which the dispensing tube is moved, from a state of non-contact with the balloon, in a direction intersecting an extending direction of the dispensing tube, and an opening portion-formed end portion side of the dispensing tube formed at its end portion with an opening portion for discharging the coating solution is thereby placed in contact with the outer surface of the balloon.

In the positioning method for balloon coating configured as above, the opening portion-formed end portion side of the dispensing tube is put in contact with the outer surface of the balloon by moving the dispensing tube in a direction intersecting the extending direction of the dispensing tube. Therefore, the burden on the balloon is relatively light, as compared to the case where the dispensing tube is brought into contact with the balloon in a colliding manner by moving the dispensing tube in the extending direction. For this reason, the dispensing tube and the balloon contact with each other in a suitable state, and the morphological form and size of the drug contained in the coating layer can be freely set. In addition, since the burden on the balloon is reduced, it is unnecessary to provide an operating step for checking whether or not the balloon has been deformed or damaged. Consequently, workability can be enhanced.

The positioning method for balloon coating may further include an application step in which the coating solution is discharged through the opening portion and applied to the outer surface of the balloon while the dispensing tube is moved relative to the balloon in an axial direction of the balloon. In this case, the coating solution can be applied to the balloon which is inhibited from being deformed or damaged in the positioning step. Therefore, the quantity and thickness of the coating solution applied to the balloon can be set with relatively high accuracy. Consequently, the morphological form and size of the drug contained in the coating layer can be set more freely.

In the positioning step, the dispensing tube may be moved in an extending direction of the dispensing tube without making contact with the balloon, after which the dispensing tube may be moved in a direction intersecting the extending direction of the dispensing tube, and the opening portion for discharging the coating solution-formed end portion side of the dispensing tube may be thereby placed in contact with the outer surface of the balloon. In this case, the dispensing tube does not contact the balloon when moved in the extending direction of the dispensing tube, and, therefore, the burden on the balloon is reduced. For this reason, it is unnecessary to provide an operating step for checking whether or not the balloon has been deformed or damaged. Consequently, workability can be enhanced.

The coating solution may be discharged in a state where a continuous length of a side surface on the opening portion-formed end portion side of the dispensing tube is kept in contact with the outer surface of the balloon. In this case, suitable contact can be given between the dispensing tube and the balloon such that the crystals of the water-insoluble drug assume a morphological form that includes a plurality of elongate bodies having each independent long axis.

In the case where a plane which is perpendicular to the extending direction of the dispensing tube in a state of non-contact with the balloon and which passes through the axis of the balloon is defined as a reference plane, the dispensing tube may, in the contact step, be positioned relative to the balloon in such a manner that a virtual position at which the opening portion would be located if the dispensing tube is assumed to be non-flexible is located at a position deviated from the reference plane toward the balloon rotating direction side by an angle within the range of 0 degrees to 40 degrees, with the axis of the balloon as the vertex of the angle, in a region extending from the reference plane in a direction opposite to a discharge direction of the dispensing tube. In this case, the dispensing tube can be inhibited from slipping off from the contact position due to a frictional force between the dispensing tube and the balloon. Therefore, favorable contact can be maintained, and a desired coating layer can be formed.

In the contact step, the dispensing tube, which is flexible, may be pressed against the outer surface of the balloon while being bent. In this case, it is ensured that even if the balloon becomes eccentric, the dispensing tube moves following up to the balloon, so that the balloon can be inhibited from being damaged, and favorable contact of the dispensing tube with the balloon can be maintained. Consequently, the morphological form, size and the like of the drug contained in the coating layer can be set more freely.

In addition, a balloon coating method is disclosed for forming a coating layer containing a water-insoluble drug on an outer surface of a balloon of a balloon catheter, the balloon coating method including an application step in which, where a flexible dispensing tube for supplying a coating solution containing the water-insoluble drug and a solvent is formed at its end portion with an opening portion for discharging the coating solution therethrough and when the opening portion-formed end portion side of the dispensing tube is kept in contact with the outer surface of the balloon in such a manner as to be oriented in a direction opposite to a rotating direction of the balloon while the balloon is rotated about an axis of the balloon, the coating solution is discharged through the opening portion and applied to the outer surface of the balloon while the dispensing tube is moved relative to the balloon in an axial direction of the balloon.

In the balloon coating method configured as above, the coating solution is discharged while the dispensing tube is kept in contact with the outer surface of the balloon in such a manner that the opening portion of the dispensing tube is oriented in the direction opposite to the rotating direction of the balloon. By giving suitable contact between the dispensing tube and the balloon, therefore, the morphological form, size and the like of the drug contained in the coating layer can be set more freely. Particularly, for example, by discharging the coating solution while the opening portion of the dispensing tube is in contact with the outer surface of the balloon so as to be oriented in the direction opposite to the rotating direction of the balloon, the water-insoluble drug in the coating layer formed on the outer surface of the balloon can be formed in a morphological form including a plurality of elongate bodies having each independent long axes of the crystal.

In the application step, the coating solution may be discharged in a state where a continuous length of a side surface on the opening portion-formed end portion side of the dispensing tube is in contact with the outer surface of the balloon. In this case, suitable contact can be given between the dispensing tube and the balloon, such that the crystals of the water-insoluble drug assume a morphological form including a plurality of elongate bodies having each independent long axis.

In the application step, the coating solution may be discharged, with the flexible dispensing tube being pressed against the outer surface of the balloon while being bent. In this case, it is ensured that even if the balloon becomes eccentric, the dispensing tube moves following up to the balloon; therefore, the balloon can be inhibited from being damaged, and the contact of the dispensing tube with the balloon can be maintained favorably. Consequently, the thickness and morphological form of the coating layer formed can be set with high accuracy.

In the application step, the coating solution may be discharged through the opening portion while the dispensing tube is kept in contact with that portion of the balloon which is rotating toward an upper side in the vertical direction. In this case, it can be relatively easy to dispose the dispensing tube in such a manner that the opening portion is oriented in the direction opposite to the rotating direction of the balloon.

The water-insoluble drug may be rapamycin, paclitaxel, docetaxel, or everolimus. In this case, restenosis of a stenosed part in a blood vessel can be favorably inhibited by the aforementioned water-insoluble drug formed the crystals of which assume a morphological form including a plurality of elongate bodies having each independent long axes.

In addition, another balloon coating method according to the present disclosure is a balloon coating method for forming a coating layer containing a water-insoluble drug on an outer surface of a balloon of a balloon catheter, the balloon coating method including an application step in which, where a pipe-shaped dispensing tube formed from a polyolefin for supplying a coating solution containing the water-insoluble drug and a solvent is formed at its end portion with an opening portion for discharging the coating solution therethrough and when the opening portion-formed end portion side of the dispensing tube is placed in contact with the outer surface of the balloon while the balloon is rotated about an axis of the balloon, the coating solution is discharged through the opening portion and applied to the outer surface of the balloon while the dispensing tube is moved relative to the balloon in an axial direction of the balloon. In the balloon coating method configured as above, the dispensing tube formed from the polyolefin is placed in contact with the balloon, and, therefore, the affinity of the dispensing tube for the solvent is high and the contact angle is small, as compared to the case where a fluororesin-made tube is used. For this reason, the coating solution is less liable to be repelled at the opening portion of the dispensing tube and at the part of contact with the balloon, so that unevenness of coating with the coating solution is less liable to be generated on the outer surface of the balloon. Consequently, the degree of uniformity of the coating layer can be regulated with high accuracy, and the morphological form, size and the like of the drug contained in the coating layer can be set more freely.

The dispensing tube may be formed from polyethylene or polypropylene. In this case, the affinity of the dispensing tube for organic solvents can be securely enhanced and the contact angles can be securely reduced, as compared to the case of a fluororesin-made tube.

In the application step, the coating solution may be discharged in a state where a continuous length of a side surface on the opening portion-formed end portion side of the dispensing tube is in contact with the outer surface of the balloon. In this case, a suitable contact can be given between the dispensing tube and the balloon, such that the crystals of the water-insoluble drug assume a morphological form including a plurality of elongate bodies having each independent long axis.

In addition, a coating layer control method according to the present disclosure is a coating layer control method for controlling the degree of uniformity of a coating layer that contains a water-insoluble drug and is formed on an outer surface of a balloon of a balloon catheter, the coating layer control method including an application step in which, where a pipe-shaped dispensing tube formed from a polyolefin for supplying a coating solution containing the water-insoluble drug and a solvent is formed at its end portion with an opening portion for discharging the coating solution therethrough and when the opening portion-formed end portion side of the dispensing tube is placed in contact with the outer surface of the balloon while the balloon is rotated about an axis of the balloon, the coating solution is discharged through the opening portion and applied to the outer surface of the balloon while the dispensing tube is moved relative to the balloon in an axial direction of the balloon. In the coating layer control method configured as above, the dispensing tube formed from the polyolefin is placed in contact with the balloon, and, therefore, the affinity of the dispensing tube for the solvent is high and the contact angle is small, as compared to the case where a fluororesin-made tube is used. For this reason, the coating solution is less liable to be repelled at the opening portion of the dispensing tube and at the part of contact with the balloon, so that unevenness of coating with the coating solution is less liable to be generated on the outer surface of the balloon. Consequently, the degree of uniformity of the coating layer can be controlled with high accuracy, and the morphological form, size and the like of the drug contained in the coating layer can be set more freely.

In the application step, the dispensing tube formed from the resin may be formed from a polyolefin or a fluororesin, and the degree of uniformity of the coating layer may be controlled by use of the dispensing tube. In this case, while enhancing the degree of uniformity of the coating layer by use of the dispensing tube formed from the polyolefin, unevenness of coating can be imparted to the coating layer by use of another dispensing tube formed from a fluororesin. Consequently, the level of the degree of uniformity of the coating layer can be controlled arbitrarily.

In the application step, the degree of uniformity of the coating layer may be controlled by regulating at least one of the moving speed of the dispensing tube relative to the balloon in the axial direction, the discharge rate of the coating solution from the dispensing tube, and the rotating speed of the balloon. In this case, the level of the degree of uniformity of the coating layer can be controlled arbitrarily.

In addition, a balloon coating apparatus according to the present disclosure is a balloon coating apparatus for forming a coating layer containing a water-insoluble drug on an outer surface of a balloon catheter. The balloon coating apparatus includes a rotation mechanism portion for rotating the balloon about an axis of the balloon, a pipe-shaped dispensing tube formed from a polyolefin for supplying a coating solution containing the water-insoluble drug and a solvent, and a movement mechanism portion for moving the dispensing tube relative to the balloon in an axial direction of the balloon. In the balloon coating apparatus configured as above, the dispensing tube is formed from a polyolefin, and, therefore, its affinity for the solvent is high and the contact angle is small, as compared with a fluororesin-made tube. For this reason, the coating solution is less liable to be strongly repelled at the opening portion of the dispensing tube or at the part of contact with the balloon, so that unevenness of coating with the coating solution is less liable to be generated on the outer surface of the balloon. Consequently, the degree of uniformity of the coating layer can be controlled with high accuracy, and the morphological form, size and the like of the drug contained in the coating layer can be set more freely.

In addition, a further balloon coating method according to the present disclosure is a balloon coating method for forming a coating layer containing a water-insoluble drug on an outer surface of a balloon of a balloon catheter in such a manner that the coating layer has regular unevenness. The balloon coating method includes an application step in which, where a pipe-shaped dispensing tube formed from a fluororesin for supplying a coating solution containing the water-insoluble drug and a solvent is formed at its end portion with an opening portion for discharging the coating solution therethrough and when the opening portion-formed end portion side of the dispensing tube is kept in contact with the outer surface of the balloon, the coating solution is discharged through the opening portion and applied to the outer surface of the balloon while the dispensing tube is moved relative to the balloon in an axial direction of the balloon and while the balloon is exposed through gaps between portions of the coating solution. In the balloon coating method configured as above, the dispensing tube formed from the fluororesin is placed in contact with the balloon, and, therefore, the affinity of the dispensing tube for the solvent is low and the contact angle is large. For this reason, the coating solution is strongly repelled at the opening portion of the dispensing tube and at the part of contact with the balloon. Accordingly, it can be relatively easy to apply the coating solution to the balloon while exposing the balloon through the gaps between the applied portions of the coating solution. Consequently, the morphological form and size of the drug contained in the coating layer can be set more freely.

In the application step, the coating solution may be discharged in a state where a continuous length of a side surface on the opening portion-formed end portion side of the dispensing tube is kept in contact with the outer surface of the balloon. In this case, suitable contact can be given between the dispensing tube and the balloon such that the crystals of the water-insoluble drug assume a morphological form that includes a plurality of elongate bodies having each independent long axis.

In the application step, the coating solution may be applied to the outer surface of the balloon in such a manner as to form a spiral linear body. In this case, by applying the coating solution while the balloon is rotated relative to the dispensing tube, a coating layer having gaps through which the balloon is exposed can be formed relatively easily.

In addition, a positioning method for balloon coating according to the present disclosure is a positioning method for balloon coating for forming a coating layer containing a water-insoluble drug on an outer surface of a balloon of a balloon catheter, wherein a flexible dispensing tube is formed with an opening portion for discharging a coating solution containing the water-insoluble drug and a solvent, and a plane which is perpendicular to an extending direction of the dispensing tube in a state of non-contact with the balloon and which passes through an axis of the balloon is defined as a reference plane; and the positioning method includes a positioning step in which the dispensing tube is positioned relative to the balloon in such a manner that a virtual position at which the opening portion would be located if the dispensing tube is assumed to be non-flexible is located at a position deviated from the reference plane toward the balloon rotating direction side by an angle within the range of 0 degrees to 40 degrees, with the axis of the balloon as the vertex of the angle, in a region extending from the reference plane in a direction opposite to a discharge direction of the dispensing tube. In the positioning method for balloon coating configured as above, the dispensing tube is positioned relative to the balloon in such a manner as to be located within a range of 0 degrees to 40 degrees from the reference plane toward the rotating direction side of the balloon, with the axis of the balloon as the vertex of the angle. Therefore, the dispensing tube can be inhibited from slipping off from the contact position due to a frictional force between the dispensing tube and the balloon, and favorable contact is maintained. Consequently, the morphological form and size of the water-insoluble drug contained in the coating layer can be freely set.

The positioning method for balloon coating may further include an application step in which the coating solution is discharged through the opening portion and applied to the outer surface of the balloon while the dispensing tube is moved relative to the balloon in an axial direction of the balloon. In this case, the coating solution can be applied to the balloon by the dispensing tube, which is maintained in favorable contact with the balloon in the positioning step. Therefore, the quantity and thickness of the coating solution applied to the balloon can be set with relative high accuracy. Consequently, the morphological form and size of the drug contained in the coating layer can be set more freely.

In the positioning step, the dispensing tube may be moved in the extending direction of the dispensing tube without making contact with the balloon, after which the dispensing tube may be moved in a direction intersecting the extending direction of the dispensing tube, and an opening portion for discharging the coating solution-formed end portion side of the dispensing tube formed with the opening portion at its end portion may be thereby placed in contact with the outer surface of the balloon. In this case, the dispensing tube does not contact the balloon when moved in the extending direction of the dispensing tube, so that the burden on the balloon is reduced. Therefore, it is unnecessary to provide an operating step for checking whether or not the balloon has been deformed or damaged. Consequently, workability can be enhanced.

The coating solution may be discharged in a state where a continuous length of a side surface on the opening portion-formed end portion side of the dispensing tube is kept in contact with the outer surface of the balloon. In this case, suitable contact can be given between the dispensing tube and the balloon such that the crystals of the water-insoluble drug assume a morphological form that includes a plurality of elongate bodies having each independent long axis.

In the contact step, the flexible dispensing tube may be pressed against the outer surface of the balloon while being bent. In this case, it can be relatively ensured that even if the balloon becomes eccentric, the dispensing tube moves following up to the balloon, so that the balloon can be inhibited from being damaged, and favorable contact of the dispensing tube with the balloon can be maintained. Consequently, the morphological form and size of the drug contained in the coating layer can be set more freely.

In accordance with an exemplary embodiment, a method is disclosed for forming a coating layer on an outer surface of a balloon of a balloon catheter, the method comprising: supplying a coating solution containing a drug and a solvent through an end portion of a flexible dispensing tube with an opening portion for discharging the coating solution through the end portion of the flexible dispensing tube; keeping in contact an opening portion-formed end portion side of the flexible dispensing tube with the outer surface of the balloon in such a manner as to be oriented in a direction opposite to a rotating direction of the balloon; rotating the balloon about an axis of the balloon; and discharging the coating solution through the opening portion and applying the coating solution to the outer surface of the balloon while the flexible dispensing tube is moved relative to the balloon in an axial direction of the balloon.

In accordance with another exemplary embodiment, a balloon coating method is disclosed for forming a coating layer on an outer surface of a balloon of a balloon catheter, the balloon coating method comprising: an application step in which, where a flexible dispensing tube for supplying a coating solution containing a drug and a solvent is formed at an end portion of the flexible dispensing tube with an opening portion for discharging the coating solution through the opening portion and when an opening portion-formed end portion side of the flexible dispensing tube is kept in contact with the outer surface of the balloon in such a manner as to be oriented in a direction opposite to a rotating direction of the balloon while the balloon is rotated about an axis of the balloon, the coating solution is discharged through the opening portion and applied to the outer surface of the balloon while the flexible dispensing tube is moved relative to the balloon in an axial direction of the balloon.

BRIEF DESCRIPTION OF DRAWINGS

FIGS. 6A and 6B show sectional views illustrating modifications of a contact position where the dispensing tube contacts the balloon, wherein FIG. 6A shows a case where a discharge direction of the dispensing tube is the same as the rotating direction of the balloon, while FIG. 6B shows a case where the discharge direction of the dispensing tube is perpendicular to an outer circumferential surface of the balloon.

FIG. 31 is a view showing, in terms of coordinates, positions of contact of a dispensing tube with a balloon.

FIGS. 32A-32C show pictures obtained by photographing a surface of a balloon produced in Example 10, wherein FIG. 32A shows a proximal portion, FIG. 32B shows a central portion, and FIG. 32C shows a distal portion.

FIGS. 33A-33C show pictures obtained by photographing a surface of a balloon produced in Example 11, wherein FIG. 33A shows a proximal portion, FIG. 33B shows a central portion, and FIG. 33C shows a distal portion.

FIGS. 34A-34C show pictures obtained by photographing a surface of a balloon produced in Example 12, wherein FIG. 34A shows a proximal portion, FIG. 34B shows a central portion, and FIG. 34C shows a distal portion.

FIGS. 35A-35C show pictures obtained by photographing a surface of a balloon produced in Example 13, wherein FIG. 35A shows a proximal portion, FIG. 35B shows a central portion, and FIG. 35C shows a distal portion.

FIGS. 36A-36C show pictures obtained by photographing a surface of a balloon produced in Example 14, wherein FIG. 36A shows a proximal portion, FIG. 36B shows a central portion, and FIG. 36C shows a distal portion.

FIGS. 37A-37C show pictures obtained by photographing a surface of a balloon produced in Example 15, wherein FIG. 37A shows a proximal portion, FIG. 37B shows a central portion, and FIG. 37C shows a distal portion.

FIGS. 38A-38C show pictures obtained by photographing a surface of a balloon produced in Comparative Example 5, wherein FIG. 38A shows a proximal portion, FIG. 38B shows a central portion, and FIG. 38C shows a distal portion.

DETAILED DESCRIPTION

Figure 1:
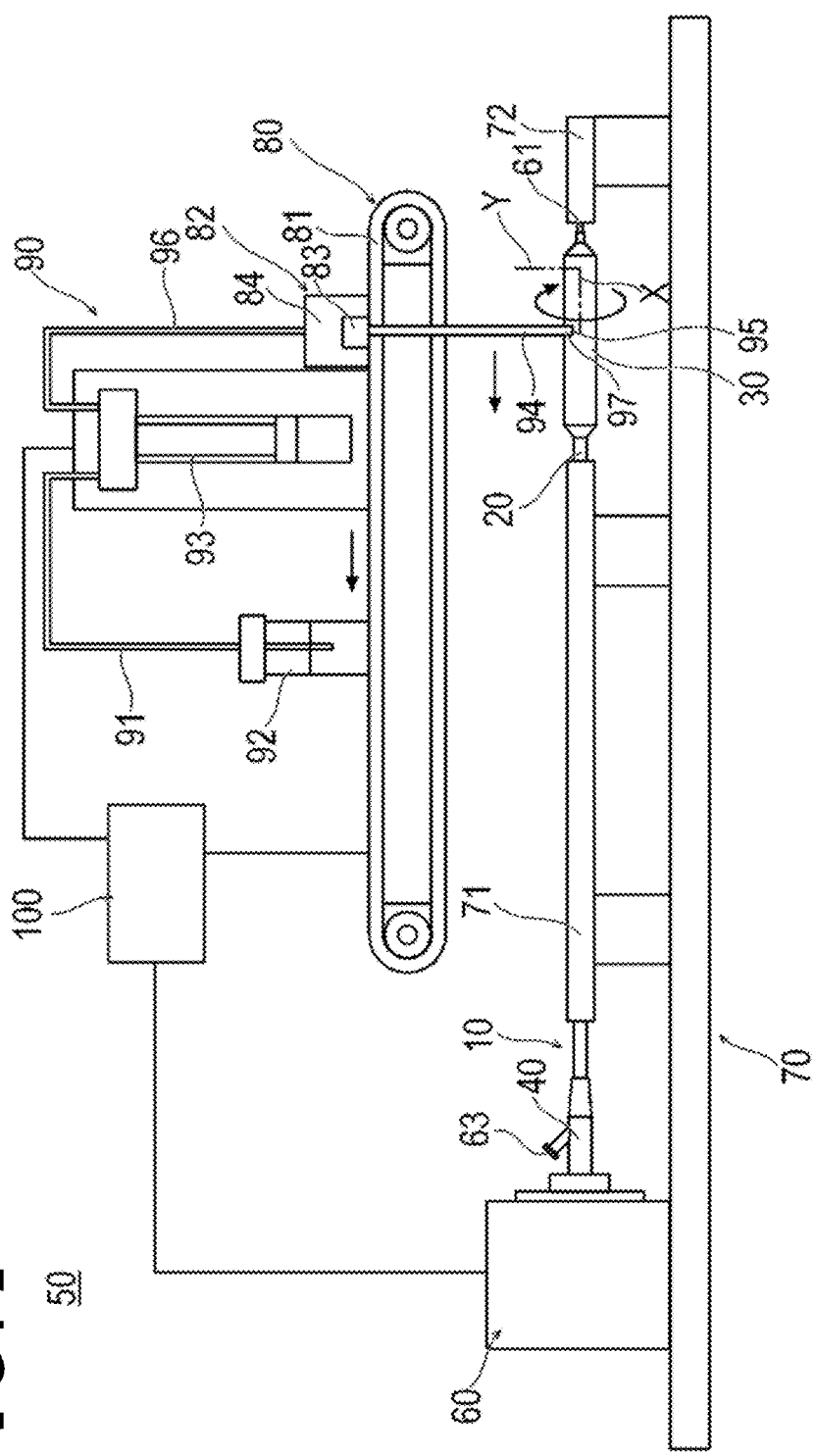
FIG. 1 is a schematic view showing an apparatus for carrying out a balloon coating method according to an embodiment.

Referring to the drawings, embodiments of the present disclosure will now be described below. Note that the dimensional ratios in the drawings may be exaggerated and different from the actual ratios, for convenience of explanation.

A balloon coating method according to an embodiment of the present disclosure is for forming a coating layer containing a water-insoluble drug on a surface of a balloon, and is carried out by a balloon coating apparatus 50 illustrated in FIG. 1. Note that, in the present specification, the side on which a balloon catheter 10 is inserted into a body lumen will be referred to as "distal" or "distal side," whereas the operator's hand side on which the balloon catheter 10 is operated will be referred to as "proximal" or "proximal side."

Figure 2:
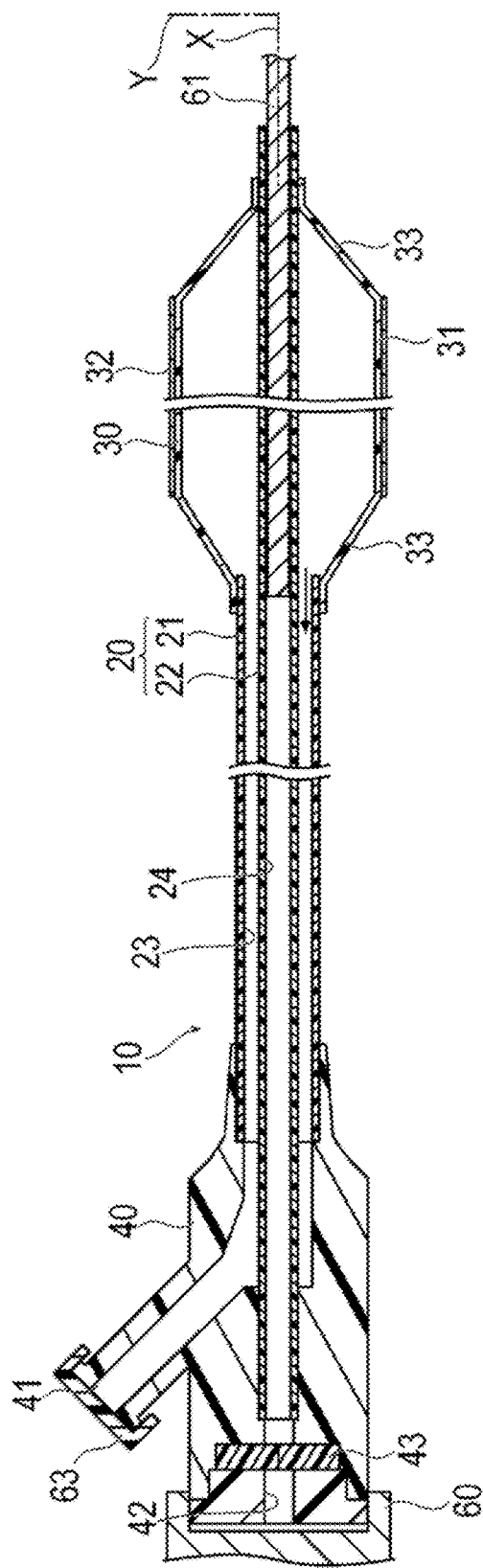
FIG. 2 is a sectional view showing a balloon catheter.

First, the structure of the balloon catheter 10 will be described. As illustrated in FIG. 2, the balloon catheter 10 can include an elongated catheter main body portion 20, a balloon 30 provided at a distal portion of the catheter main body portion 20, and a hub 40 firmly attached to a proximal of the catheter main body portion 20.

The catheter main body portion 20 can include an outer tube 21 which is a pipe-shaped body opening at a distal and a proximal of the catheter main body portion 20, and an inner tube 22 disposed inside the outer tube 21. Between the outer tube 21 and the inner tube 22 is formed an expansion lumen 23 through which an expansion fluid for expanding (inflating) the balloon 30 flows. In addition, inside the inner tube 22 is formed a guide wire lumen 24 into and through which a guide wire is inserted and passed.

The balloon 30 is adhered to the inner tube 22 on the distal side, and is adhered to the outer tube 21 on the proximal side, with the inside of the balloon 30 communicating with the expansion lumen 23. At a central portion in an axial direction X of the balloon 30, is formed a cylindrical straight portion 31 (expansion portion) having a constant outer diameter when expanded. On both sides in the axial direction X of the straight portion 31, are formed tapered portions 33 where the outside diameter varies gradually. A coating layer 32 containing a drug is formed over the whole area of the outer surface of the straight portion 31. Note that the range over which the balloon 30 is formed with the coating layer 32 is not limited only to the straight portion 31. Thus, the range may include at least part of the tapered portions 33 in addition to the straight portion 31, or may be only part of the straight portion 31.

The hub 40 can include a first opening portion 41 which communicates with the expansion lumen 23 of the outer tube 21 and which functions as a port through which the expansion fluid is let flow in and out, and a second opening portion 42 into and through which the guide wire lumen 24 is inserted and passed. At the second opening portion 42, there is provided a blood stop valve 43 for inhibiting blood from flowing out.

The balloon 30 preferably has a certain degree of flexibility and a certain degree of hardness such that the drug can be released from the coating layer 32 provided thereon when the balloon 30 is expanded upon arrival at a blood vessel or tissue. Specifically, for example, the balloon 30 is formed from metal or resin. It is preferable that at least the surface of the balloon 30 on which to provide the coating layer 32 is formed of resin. Examples of the material which can be used for forming at least the surface of the balloon 30 include thermoplastic resins such as polyolefins (for example, polyethylene, polypropylene, polybutene, ethylene-propylene copolymers, ethylene-vinyl acetate copolymers, ionomers, or mixtures of two or more of them), flexible polyvinyl chloride resin, polyamides, polyamide elastomers, polyester, polyester elastomers, polyurethane, and fluororesins, silicone rubbers, or latex rubbers. Among these, preferred, for example, are the polyamides. Specifically, at least part of the surface of the expansion portion of the medical device to be coated with the drug is made of a polyamide. The polyamide is not particularly limited so long as it is a polymer, which has an amide linkage. Examples of the polyamide include homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), and polydodecanolactam (nylon 12), copolymers such as caprolactam/lauryllactam copolymer (nylon 6/12), caprolactam/aminoundecanoic acid copolymer (nylon 6/11), caprolactam/w-aminononanoic acid copolymer (nylon 6/9), and caprolactam/hexamethylenediammonium adipate copolymer (nylon 6/66), and aromatic polyamides such as copolymers of adipic acid with metaxylenediamine, or copolymers of hexamethylenediamine with m,p-phthalic acid. Further, polyamide elastomers wherein nylon 6, nylon 66, nylon 11, or nylon 12 constitutes hard segments and a polyalkylene glycol, a polyether, an aliphatic polyester or the like constitutes soft segments can also be used as a base material of the medical device according to the present disclosure. The previously mentioned polyamides may be used either singly or in combination of two or more of them.

The balloon 30 is formed, over a surface of the base material thereof, with the coating layer 32 either directly or through a pretreatment layer such as a primer layer therebetween by a coating method which will be described later.

The balloon coating apparatus 50 will now be described. As depicted in FIG. 1, the balloon coating apparatus 50 can include a rotation mechanism portion 60 which holds the balloon catheter 10 and rotates the balloon catheter 10 about an axis X of the balloon 30, a support base 70 which supports the balloon catheter 10, an application mechanism portion 90 provided with a dispensing tube 94 for applying a coating solution to an outer surface of the balloon 30, a movement mechanism portion 80 for moving the dispensing tube 94 relative to the balloon 30, and a control unit 100 for controlling the balloon coating apparatus 50.

The rotation mechanism portion 60 holds the hub 40 of the balloon catheter 10, and rotates the balloon catheter 10 by a drive source such as a motor incorporated therein. The balloon catheter 10 is held with a core member 61 inserted in the guide wire lumen 24, and the coating solution is prevented by the core member 61 from flowing into the guide wire lumen 24. In addition, the balloon catheter 10 is configured in such a manner that when the balloon 30 is expanded, the expansion fluid can be sealed with a cap 63 put on the first opening portion 41 of the hub 40 such as to cover the expansion lumen 23.

The support base 70 can include a pipe-shaped proximal-side support portion 71, which accommodates and rotatably supports the catheter main body portion 20 therein, and a distal-side support portion 72, which supports the core member 61 in a rotatable manner. Note that, if possible, the distal-side support portion 72 may support a distal portion of the catheter main body portion 20, instead of the core member 61, in a rotatable manner.

The movement mechanism portion 80 can include a movable base 81 capable of moving rectilinearly in a direction parallel to the axis X of the balloon 30, and a tube positioning portion 82 on which the movable base 81 is also placed and which is for moving the dispensing tube 94 in a Y-axis direction and a Z-axis direction (see FIG. 5) both orthogonal to the axis X. The movable base 81 can be moved rectilinearly by a drive source such as a motor incorporated therein. The application mechanism portion 90 is mounted on the movable base 81, and the movable base 81 moves the application mechanism portion 90 rectilinearly in both directions along the axis X of the balloon catheter 10. The tube positioning portion 82 can include a tube fixing portion 83 to which the dispensing tube 94 is fixed, and a driving portion 84 for moving the tube fixing portion 83 in the Y-axis direction and the Z-axis direction. The driving portion 84 is provided for example with a biaxial slider structure capable of movement by a drive source such as motors or cylinders incorporated therein so that the driving portion 84 can move the tube fixing portion 83 in both the Y-axis direction and the Z-axis direction. Note that the Y-axis direction and the Z-axis direction in which the dispensing tube 94 is moved on a plane orthogonal to the axis X of the balloon catheter 10 may not necessarily be defined as the vertical direction and a horizontal direction.

The application mechanism portion 90 can include a container 92 for containing the coating solution, a liquid feed pump 93 for feeding the coating solution at an arbitrary liquid feed rate, and the dispensing tube 94 for applying the coating solution to the balloon 30.

The liquid feed pump 93 is, for example, a syringe pump. While being controlled by the control unit 100, the liquid feed pump 93 can suck in the coating solution from the container 92 through a suction tube 91 and can feed the coating solution into the dispensing tube 94 through a supply tube 96 at an arbitrary liquid feed rate. The liquid feed pump 93 is disposed on the movable base 81, and can be moved rectilinearly by movement of the movable base 81. Note that the liquid feed pump 93 is not limited to the syringe pump so long as it can feed the coating solution; for example, the liquid feed pump 93 may be a tube pump.

Figure 5:
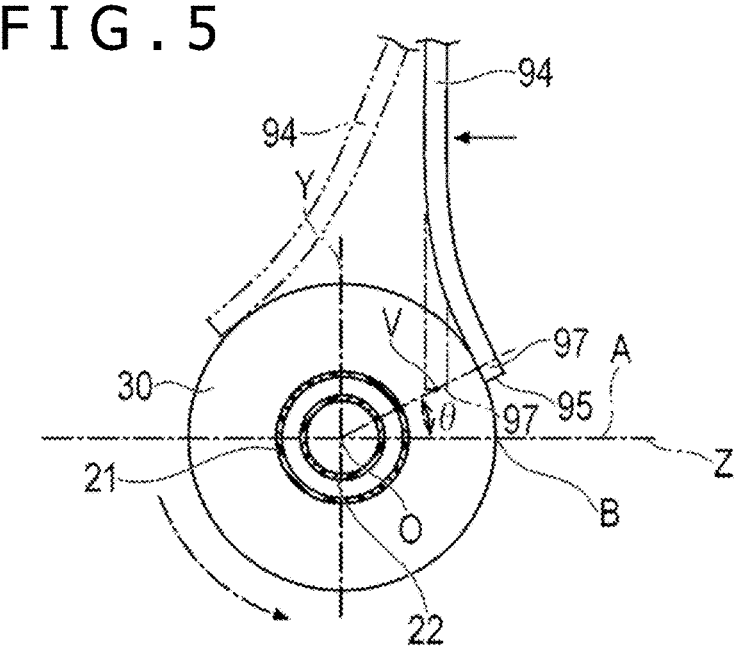
FIG. 5 is a sectional view showing a state wherein the discharge end of the dispensing tube has been moved in a Z-axis direction, in the positioning step.

The dispensing tube 94 is a member, which communicates with the supply tube 96, and through which the coating solution supplied from the liquid feed pump 93 via the supply tube 96 is discharged onto the outer surface of the balloon 30. The dispensing tube 94 is a flexible circular pipe-shaped member. The dispensing tube 94 has an upper end fixed to the tube fixing portion 83, extends vertically downward from the tube fixing portion 83, and is formed with an opening portion 95 at a discharge end 97, which is a lower end of the dispensing tube 94. By movements of the movable base 81, the dispensing tube 94 can be moved rectilinearly in both directions along the axial direction X of the balloon catheter 10, together with the liquid feed pump 93 disposed on the movable base 81. In addition, as illustrated in FIGS. 1 and 5, the dispensing tube 94 is movable in two different directions (in the present embodiment, in the Y-axis direction which is the vertical direction and in the Z-axis direction which is a horizontal direction) on a plane orthogonal to the axial direction X, and is disposed in such a manner that a portion of a side surface on the end portion side of the dispensing tube 94 (a portion of a continuous length along the extending direction of the dispensing tube 94) makes contact with the balloon outer surface. The dispensing tube 94 is capable of supplying the coating solution therethrough onto the outer surface of the balloon 30 in the state of being pressed against the balloon 30 and bent. Alternatively, a configuration may be adopted wherein the end portion side of the distal of the dispensing tube 94 is preliminarily shaped and bent in such a manner as to form a certain angle in relation to the long axis of the dispensing tube 94, and the dispensing tube 94 is disposed in such a manner that a side surface of the distal of the dispensing tube 94 thus bent or at least part of the side surface makes contact with the balloon outer surface. In this case, the discharge end exists at the distalmost end of the dispensing tube 94.

Note that the dispensing tube 94 may not necessarily be circular pipe-shaped, so long as it is capable of supplying the coating solution therethrough. In addition, the dispensing tube 94 may not necessarily extend in the vertical direction, so long as it is capable of discharging the coating solution through the opening portion 95.

The dispensing tube 94 is preferably formed of a flexible material such that contact burden on the balloon 30 can be reduced and variations in contact position attendant on rotation of the balloon 30 can be absorbed by flexure of the dispensing tube 94. Examples of the applicable constituent material of the dispensing tube 94 include polyolefins such as polyethylene or polypropylene, cyclic polyolefins, polyesters, polyamides, polyurethane, and fluoro-resins such as PTFE (polytetrafluoroethylene), ETFE (tetrafluoroethylene-ethylene copolymer), PFA (tetrafluoroethylene-perfluoroalkyl vinyl ether copolymer), and FEP (tetrafluoroethylene-hexafluoropropylene copolymer). However, the constituent material is not particularly limited, so long as it is flexible and deformable.

The outside diameter of the dispensing tube 94 is not particularly limited, and may be, for example, 0.1 mm to 5.0 mm, preferably 0.15 mm to 3.0 mm, and more preferably 0.3 mm to 2.5 mm. The inside diameter of the dispensing tube 94 is not specifically restricted, and may be, for example, 0.05 mm to 3.0 mm, preferably 0.1 mm to 2.0 mm, and more preferably 0.15 mm to 1.5 mm. The length of the dispensing tube 94 is not particularly limited, but is preferably up to 5 times the balloon diameter. The length may be, for example, 1.0 mm to 50 mm, preferably 3 mm to 40 mm, and more preferably 5 mm to 35 mm.

The control unit 100 may be composed, for example, of a computer, and generally controls the rotation mechanism portion 60, the movement mechanism portion 80, and the application mechanism portion 90. Therefore, the control unit 100 can generally control the rotational speed of the balloon 30, the initial positioning of the dispensing tube 94 in relation to the balloon 30, the moving speed of the dispensing tube 94 in the axial direction X relative to the balloon 30, the discharge rate of the drug from the dispensing tube 94, etc.

The coating solution contains a water-insoluble drug and a solvent. After the coating solution is supplied onto the outer surface of the balloon 30, the solvent is volatilized, whereby the coating layer 32 having a crystal layer or an amorphous layer is formed on the outer surface of the balloon 30. The balloon 30 and the coating layer 32 can be used as a drug eluting balloon, which sustainedly releases the drug in a living body.

Water-Insoluble Drug

The water-insoluble drug means a drug, which is insoluble or difficultly soluble in water. For example, specifically, the water-insoluble drug is a drug of which the solubility in water is less than 5 mg/mL at pH 5 to pH 8. The solubility may be less than 1 mg/mL, or, further, may be less than 0.1 mg/mL. The water-insoluble drug can include fat-soluble drugs.

Some preferred examples of the water-insoluble drug include immunosuppressants, for example, cyclosporines inclusive of cyclosporine, immunoadjuvants such as rapamycin, carcinostatics such as paclitaxel, antiviral agents or antibacterial agents, antineoplastic agents, analgesic agents and anti-inflammatory agents, antibiotics, antiepileptics, anxiolytic agents, antiparalytic agents, antagonists, neuron blocking agents, anticholinergic agents and cholinergic agents, muscarine antagonists agents and muscarine agents, antiadrenergic agents, antiarrhythmic agents, antihypertensive agents, hormone preparations, and nutritional supplements.

The water-insoluble drug is preferably at least one selected from the group consisting of rapamycin, paclitaxel, docetaxel, and everolimus. The rapamycin, paclitaxel, docetaxel, and everolimus in the present specification include their analogs and/or derivatives so long as the analogs and/or derivatives have equivalent drug activity to the original. For example, paclitaxel and docetaxel are in an analog relation. Rapamycin and everolimus are in a derivative relation. Among these, more preferable is paclitaxel.

The water-insoluble drug may further contain an excipient. The excipient is not particularly restricted so long as it is pharmaceutically acceptable. Examples of the excipient include water-soluble polymers, sugars, contrast agents, citric acid esters, amino acid esters, glycerol esters of short-chain monocarboxylic acids, and salts and surfactants that are pharmaceutically acceptable.

The excipient is preferably small in amount based on the water-insoluble drug, and preferably does not form a matrix. In addition, the excipient preferably does not contain, but may contain, micelle, liposome, contrast agent, emulsifier, or surfactant. Further, the excipient preferably does not contain polymer but contains only low molecular compounds.

The solvent is not particularly limited. Tetrahydrofuran, ethanol, glycerin (also called glycerol or propane-1,2,3-triol), acetone, methanol, dichloromethane, hexane, ethyl acetate, and water can be exemplified as the solvent. Among these, preferred are mixed solvents of some of tetrahydrofuran, ethanol, acetone, and water.

The balloon coating method of forming the coating layer 32 containing the water-insoluble drug on a surface of the balloon 30 by use of the aforementioned balloon coating apparatus 50 will be described below.

First, the expansion fluid is supplied through the first opening portion 41 of the balloon catheter 10 into the balloon 30 to expand the balloon 30; in this state, the cap 63 is put on the first opening portion 41 to achieve sealing, thereby maintaining the balloon 30 in the expanded state. Note that the coating layer 32 can also be formed on the surface of the balloon 30 without expanding the balloon 30; in this case, it is unnecessary to supply the expansion fluid into the balloon 30.

Next, in a state wherein the dispensing tube 94 does not make contact with the outer surface of the balloon 30, the balloon catheter 10 is rotatably disposed on the support base 70, and the hub 40 is connected to the rotation mechanism portion 60.

Subsequently, the dispensing tube 94 is positioned in relation to the balloon 30 (positioning step). In the positioning step, first, the position of the moving table 81 is regulated, to position the dispensing tube 94 in the X-axis direction. In this instance, the dispensing tube 94 is positioned at the distalmost position for forming the coating layer 32 on the balloon 30.

Figure 3:
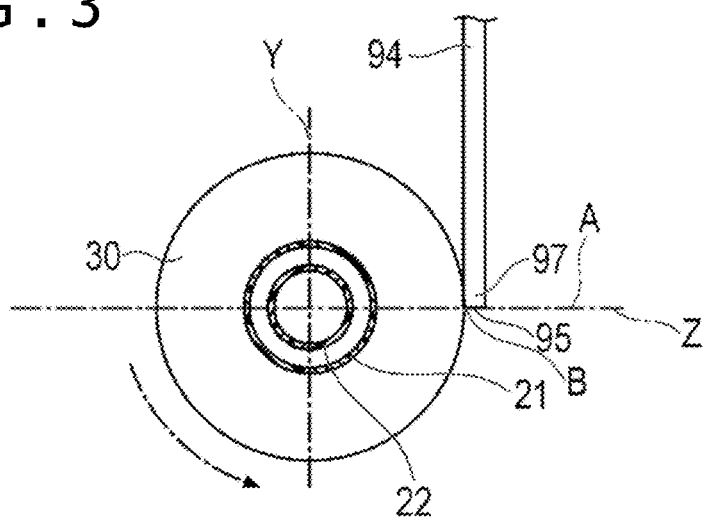
FIG. 3 is a sectional view showing a state wherein a discharge end of a dispensing tube has been positioned at a reference point of a balloon, in a positioning step.

Next, by operating the driving portion 84, the discharge end 97 of the dispensing tube 94 is positioned at a preset reference point B, in a state wherein the dispensing tube 94 is not bent, as depicted in FIG. 3. The reference point B is the position at which the outer surface of the balloon 30 is rotated in a direction (in the present embodiment, the upward direction) opposite to the discharge direction of the dispensing tube 94, on a reference plane A (in the present embodiment, a horizontal plane) which is orthogonal to the extending direction (in the present embodiment, the vertical direction) of the dispensing tube 94 and which passes through the axis X of the balloon 30. Therefore, at the position of contact between the balloon 30 and the dispensing tube 94, the balloon 30 is rotated in the direction opposite to the discharge direction in which the coating solution is discharged from the dispensing tube 94. Note that the extending direction of the dispensing tube 94 may not necessarily be the vertical direction, and the reference plane A may not necessarily be a horizontal plane.

Figure 4:
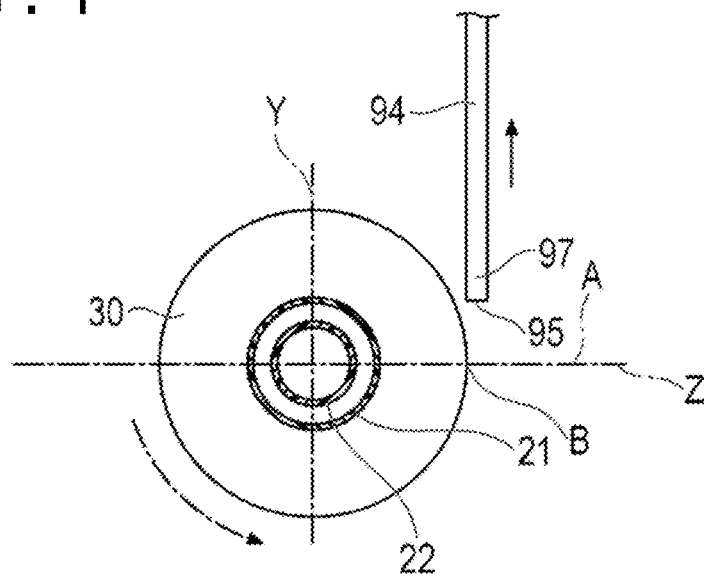
FIG. 4 is a sectional view showing a state wherein the discharge end of the dispensing tube has been moved in a Y-axis direction, in the positioning step.

Subsequently, positioning of the discharge end 97 of the dispensing tube 94 in the Y-axis direction (vertical direction) is conducted as shown in FIG. 4, by the driving portion 84. In this instance, the dispensing tube 94 can be temporarily separated from the outer surface of the balloon 30.

Next, positioning of the discharge end 97 of the dispensing tube 94 in the Z-axis direction (a horizontal direction) is performed as depicted in FIG. 5, by the driving portion 84. In this instance, the dispensing tube 94 approaches the outer surface of the balloon 30 and makes contact with the balloon 30, while being pressed against the balloon 30 and thereby bent, or without being pressed against the balloon 30 or bent. In this case, it is preferable that the length of the dispensing tube 94 is up to 5 times the balloon diameter, and the dispensing tube 94 is disposed in such a manner that its side surface on the end portion side of its distal makes contact with the balloon surface. With the dispensing tube 94 brought into contact with the balloon 30 while being moved in the Z-axis direction, the dispensing tube 94 comes into contact with the balloon 30, starting from the side of a side surface of the dispensing tube 94. Therefore, the dispensing tube 94 can bend in the manner of escaping in a direction orthogonal to the extending direction thereof, and, accordingly, there is a relatively low possibility of the balloon 30 being damaged. Alternatively, where the opening portion 95 is brought into contact with the balloon 30 in the manner of colliding against the balloon 30 while the dispensing tube 94 is being moved in the extending direction thereof, the burden on the balloon 30 is relatively heavy, so that the balloon 30 may be deformed, or the possibility cannot be denied that the balloon 30 may be damaged in some cases. Accordingly, it may become necessary to provide an operating step for checking whether or not the balloon 30 has been deformed or damaged. As mentioned above, however, the dispensing tube 94 comes into contact with the balloon 30 starting from the side of its side surface while being moved in the Z-axis direction. Therefore, it is unnecessary to provide an operating step for checking whether or not the balloon 30 has been deformed or damaged. Consequently, workability can be relatively enhanced.

In addition, the dispensing tube 94 is subjected to positioning in the Y-axis direction precedently, and is thereafter subjected to positioning in the Z-axis direction. Therefore, the dispensing tube 94 is moved in the Y-axis direction to be temporarily separated from the balloon 30, and is thereafter moved in the Z-axis direction to make contact with the balloon 30. Accordingly, the burden on the balloon 30 is lowered as compared, for example, to the case where positioning in the Z-axis direction is precedently conducted to move the dispensing tube 94 in the manner of pressing the dispensing tube 94 against the balloon 30 and, thereafter, positioning in the Y-axis direction is performed to move the dispensing tube 94 while sliding the dispensing tube 94 on the outer surface of the balloon 30. Consequently, it is unnecessary to provide an operating step for checking whether or not the balloon 30 has been deformed or damaged. Thus, workability can be relatively enhanced.

The position at which the discharge end 97 makes contact with the balloon 30 after the dispensing tube 94 is positioned is a position which is coincident with the reference plane A or a position which is deviated from the reference plane A in a direction (in the present embodiment, the upward side) opposite to the discharge direction of the dispensing tube 94, since the dispensing tube 94 is formed in a rectilinear shape. Note that in the case where the dispensing tube 94 is not rectilinear in shape, the dispensing tube 94 may make contact with the position which is deviated from the reference plane A in the discharge direction (in the present embodiment, the downward side) of the dispensing tube 94.

In accordance with an exemplary embodiment, a virtual position V at which the discharge end 97 of the dispensing tube 94 could be located if the dispensing tube 94 is assumed to be non-flexible is preferably deviated from the reference plane A by an angle θ of 0 degrees to 40 degrees in the rotating direction of the balloon 30. Note that the virtual position V is the position to which the discharge end 97 would be moved if the dispensing tube 94 were not bent when the discharge end 97 is moved from the reference point B in the Y-axis direction and the Z-axis direction by the driving portion 84. In addition, the virtual position V can be defined by only the distances the discharge end 97 is moved in the Y-axis direction and the Z-axis direction by the driving portion 84, without need to take the flexure (bending) of the dispensing tube 94 into consideration. Accordingly, the virtual position V can be controlled relatively easily.

With the deviation of the virtual position V from the reference plane A set to be within the range of 0 degrees to 40 degrees along the rotating direction of the balloon 30, the dispensing tube 94 can be restrained from slipping off from the contact position, as indicated by the alternate long and two short dashes line in FIG. 5, due to a frictional force between the dispensing tube 94 and the balloon 30, during the application step which will be described later. Specifically, where the dispensing tube 94 is in contact with the balloon 30 in such a manner that the discharge direction is opposite to the rotating direction of the balloon 30, there may arise a tendency, depending on the contact conditions, that the discharge end 97 is liable to move to a stable position at which the discharge direction of the dispensing tube 94 coincides with the rotating direction of the balloon 30. With the virtual position V located within the above-mentioned range, however, the discharge end 97 can be favorably maintained at the position at which the discharge direction is opposite to the rotating direction of the balloon 30.

Figures 6A, 6B:
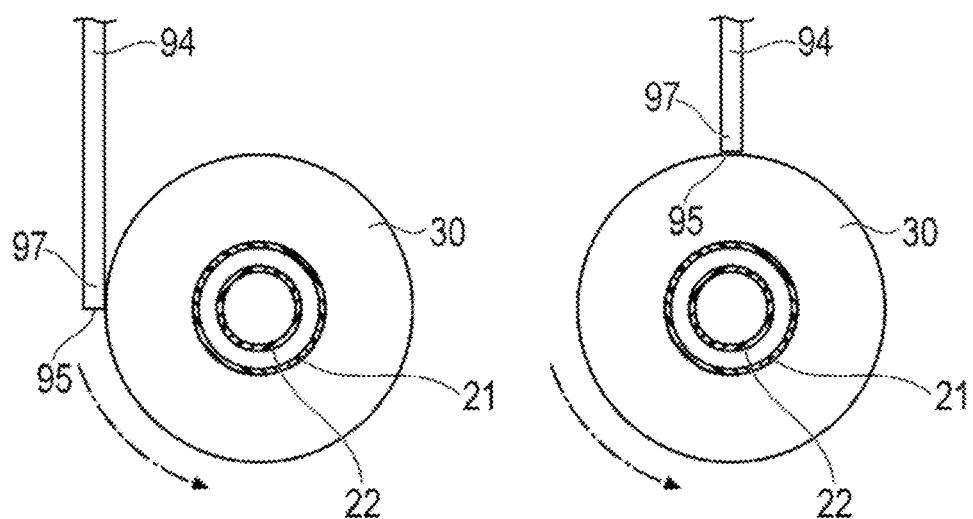
Figure 7:
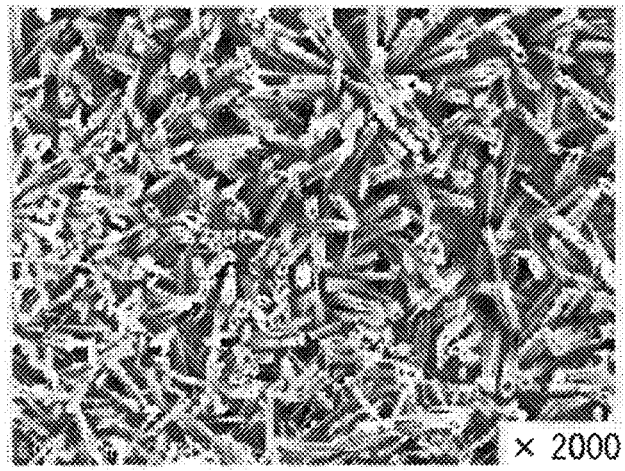
FIG. 7 is a diagram showing a scanning electron microscope (hereinafter sometimes referred to as SEM) image (2,000 times) of crystals observed at a substrate surface of a coating layer produced in Example 1.
Figure 8:
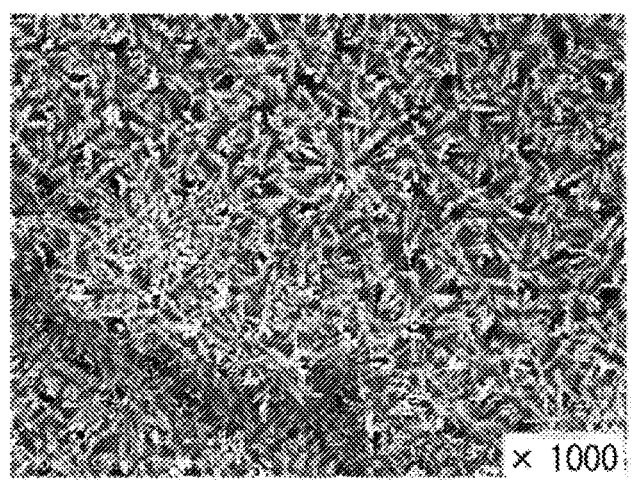
FIG. 8 is a diagram showing an SEM image (1,000 times) of the crystals observed at the substrate surface of the coating layer produced in Example 1.
Figure 9:
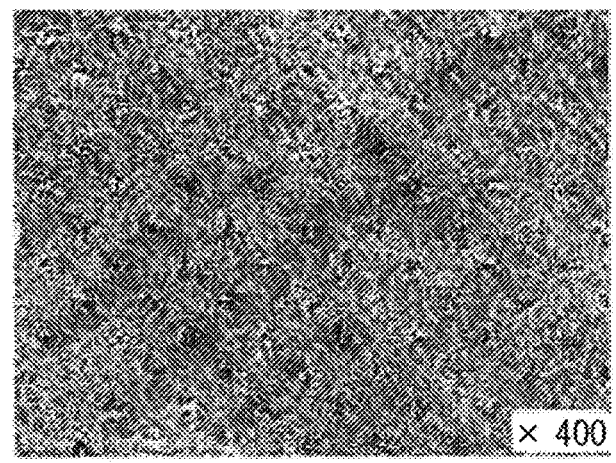
FIG. 9 is a diagram showing an SEM image (400 times) of the crystals observed at the substrate surface of the coating layer produced in Example 1.
Figure 10:
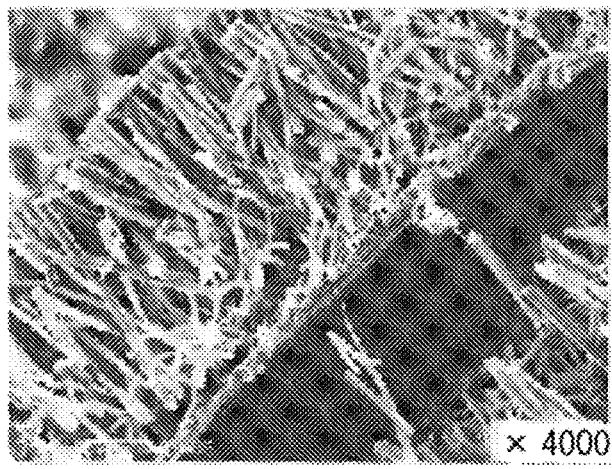
FIG. 10 is a view showing an SEM image (4,000 times) of the crystals observed at a cross-section orthogonal to the substrate surface of the coating layer produced in Example 1.
Figure 11:
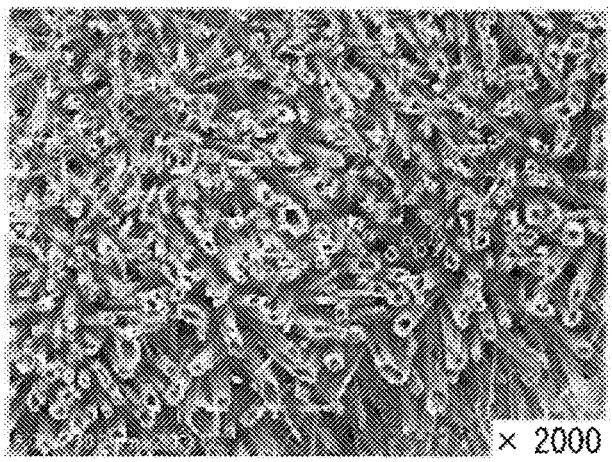
FIG. 11 is a view showing an SEM image (2,000 times) of crystals observed at a substrate surface of a coating layer produced in Example 2.
Figure 12:
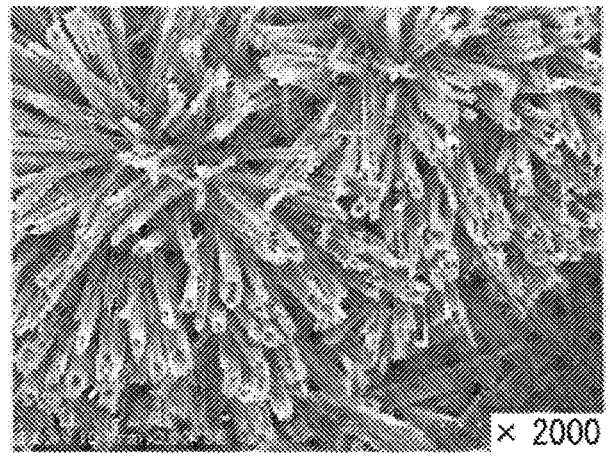
FIG. 12 is a view showing an SEM image (2,000 times) of crystals observed at a substrate surface of a coating layer produced in Example 3.
Figure 13:
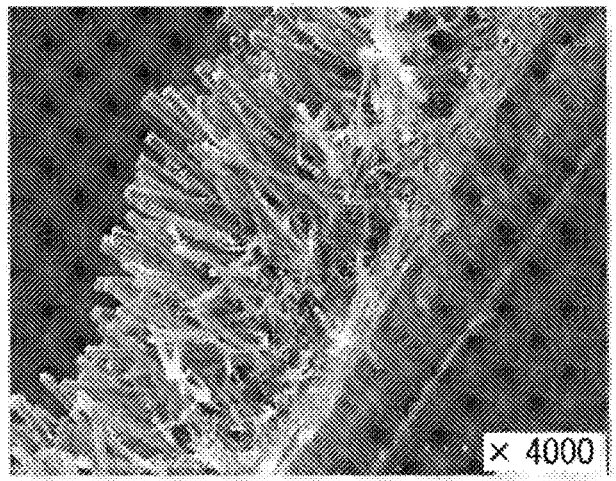
FIG. 13 is a view showing an SEM image (4,000 times) of the crystals observed at a cross-section orthogonal to the substrate surface of the coating layer produced in Example 3.
Figure 14:
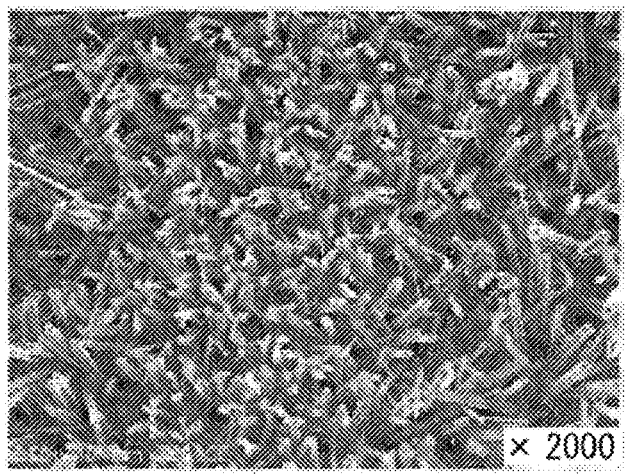
FIG. 14 is a view showing an SEM image (2,000 times) of crystals observed at a substrate surface of a coating layer produced in Example 4.
Figure 15:
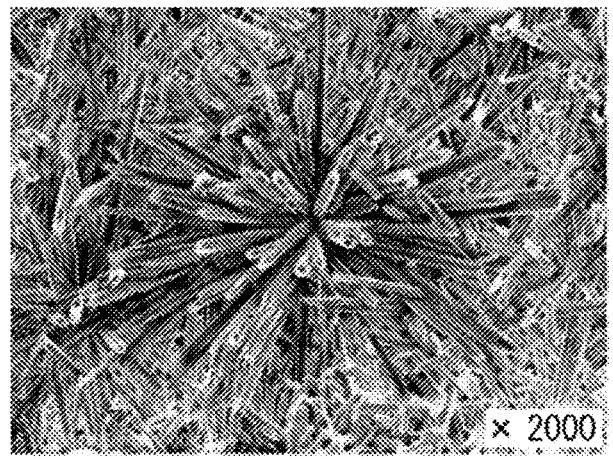
FIG. 15 is a view showing an SEM image (2,000 times) of crystals observed at a substrate surface of a coating layer produced in Example 5.
Figure 16:
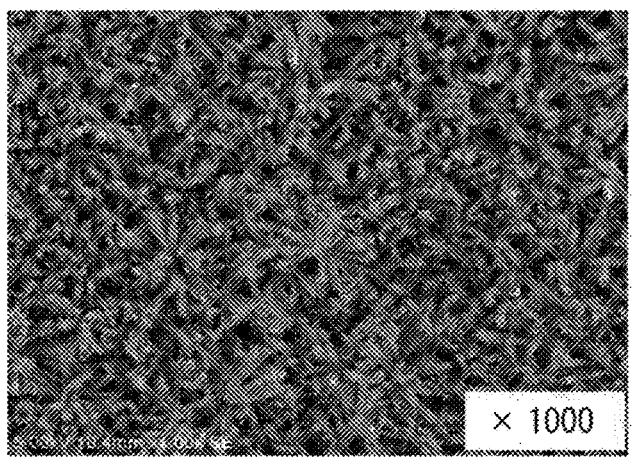
FIG. 16 is a view showing an SEM image (1,000 times) of crystals observed at a substrate surface of a coating layer produced in Example 6.
Figure 17:
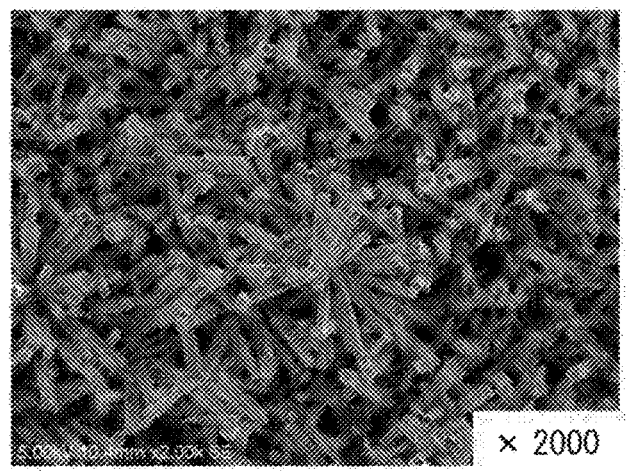
FIG. 17 is a view showing an SEM image (2,000 times) of the crystals observed at the substrate surface of the coating layer produced in Example 6.

Note that the discharge direction of the dispensing tube 94 can be set to be the same as the rotating direction of the balloon 30, as shown in FIG. 6A. In addition, the discharge direction of the dispensing tube 94 can be set to be perpendicular to the outer circumferential surface of the balloon 30, as depicted in FIG. 6B.

In addition, the step of positioning the dispensing tube 94 relative to the outer surface of the balloon 30 is not limited to the above-mentioned procedure. For example, the dispensing tube 94 may be moved in the Z-axis direction to make contact with the outer surface of the balloon 30, followed by moving the dispensing tube 94 in the Y-axis direction. In addition, the dispensing tube 94 may be moved in the Y-axis direction to thereby bring the dispensing tube 94 into contact with the outer surface of the balloon 30.

Next, the coating solution is supplied to the dispensing tube 94 while regulating the liquid feed rate by the liquid feed pump 93, the balloon catheter 10 is rotated by the rotation mechanism portion 60, and the movable base 81 is moved to thereby move the dispensing tube 94 gradually in the proximal direction along the X-direction. Since the dispensing tube 94 is moved relative to the balloon 30, the coating solution discharged from the opening portion 95 of the dispensing tube 94 is applied to the outer circumferential surface of the balloon 30 while drawing a spiral (application step). In this case, after the coating solution is applied at a position where the outer surface of the balloon 30 is rotated in a direction (in the present embodiment, the upward direction) opposite to the discharge direction of the dispensing tube 94, the part coated with the coating solution does not contact other member (for example, a dispensing tube whose discharge direction coincides with the rotating direction). Since the part coated with the coating solution does not contact, for example, a dispensing tube whose discharge direction coincides with the rotating direction, it is possible to eliminate the possibility of hampering the formation of "a morphological form wherein crystals of the water-insoluble drug include a plurality of elongate bodies having each independent long axes," and it is possible to preclude the possibility of breakage of the morphological form after the formation.

The moving speed of the dispensing tube 94 is not particularly limited, and is, for example, 0.01 mm/second to 2 mm/second, preferably 0.03 mm/second to 1.5 mm/second, and more preferably 0.05 mm/second to 1.0 mm/second. The discharge rate of the coating solution from the dispensing tube 94 is not specifically restricted, and is, for example, 0.01 μL/second to 1.5 μL/second, preferably 0.01 μL/second to 1.0 μL/second, and more preferably 0.03 μL/second to 0.8 μL/second. The rotational speed of the balloon 30 is not particularly limited, and is, for example, 10 rpm to 300 rpm, preferably 30 rpm to 250 rpm, and more preferably 50 rpm to 200 rpm. The diameter of the balloon 30 at the time of coating the balloon 30 with the coating solution is not specifically restricted, and is, for example, 1 mm to 10 mm, preferably 2 mm to 7 mm.

When the balloon catheter 10 is rotated, the balloon 30 may, in some cases, become eccentric due to bending along the axial direction X of the balloon 30. Since the dispensing tube 94 is flexible, however, even if the balloon 30 becomes eccentric, the dispensing tube 94 moves following up to the balloon 30, whereby good contact of these members is maintained. Consequently, variations in the thickness of the coating solution applied can be restrained, and it becomes relatively easy to regulate the thickness and the morphological form of the coating layer 32.

Thereafter, the solvent contained in the coating solution applied to the surface of the balloon 30 is volatilized, and the coating layer 32 containing the water-insoluble drug is formed on the surface of the balloon 30. The volatilization time is appropriately set according to the solvent, and is, for example, approximately several seconds to several hundreds of seconds.

The amount of the drug contained in the coating layer 32 is not particularly limited. The amount, in density, for example, is 0.1 μg/mm$^2$ to 10 μg/mm$^2$, preferably 0.5 μg/mm$^2$ to 5 μg/mm$^2$, more preferably 0.5 μg/mm$^2$ to 4 μg/mm$^2$, and further preferably 1.0 μg/mm$^2$ to 3.5 μg/mm$^2$.

In addition, since the extending direction toward the opening portion 95 of the dispensing tube 94 (discharge direction) is opposite to the rotating direction of the balloon 30, the water-insoluble drug in the coating layer 32 formed on the outer surface of the balloon 30 has its crystals formed to include a morphological form including a plurality of elongate bodies having each independent long axes.

The coating layer 32 wherein the crystals assume the morphological form including a plurality of elongate bodies having each independent long axes can include the plurality of elongate bodies in the state of forming mutually independent elongate body shapes on the substrate (the outer surface of the balloon 30). The plurality of elongate bodies may extend substantially outward in the circumferential direction with respect to the balloon surface, or may be arranged in directions substantially parallel to the circumferential direction. The plurality of elongate bodies may be present in the state of combination of these arrangements, or may be present in contact with each other such that the adjacent elongate bodies form different angles. The plurality of elongate bodies may be located with spaces (spaces not containing the crystal) therebetween on the balloon surface. Specifically, for example, a preferable coating layer 32 is a layer wherein a plurality of elongate bodies each composed of the crystal of the water-insoluble drug and having a long axis are present in a brush-like pattern. The plurality of elongate bodies are arranged in a circumferential and brush-like pattern on the surface of the substrate. Each of the elongate bodies is present independently, and has a certain length, with one end (proximal) of the length part being fixed to the substrate surface. The elongate body does not form a composite structure, and is not connected, with the adjacent elongate bodies. The long axis of the crystal is substantially rectilinear. The elongate body forms a predetermined angle with the substrate surface intersecting the long axis thereof. The predetermined angle here is in the range of, for example, from 45 degrees to 135 degrees, preferably 70 degrees to 110 degrees, and more preferably 80 degrees to 100 degrees. Further preferably, the long axis of the elongate body forms an angle of, for example, substantially 90 degrees with the substrate surface. The elongate body, at least its portion near the distal of the elongate body, is hollow. A section of the elongate body in a plane orthogonal (perpendicular) to the long axis of the elongate body has a void (hollow portion). In the elongate body thus having a void, the section of the elongate body in a plane orthogonal (perpendicular) to the long axis is polygonal in shape. The polygon is, for example, a tetragon, a pentagon, or a hexagon. Therefore, the elongate body is formed as an elongated polyhedron that has a distal (or distal surface) and a proximal (or proximal surface), wherein a side surface portion between the distal (or distal surface) and the proximal (or proximal surface) is composed of a plurality of substantially plain surfaces. This crystalline morphological form (hollow elongate body crystalline morphological form) constitutes the whole or at least part of a plane at the substrate surface. For example, the layer including the hollow elongate body crystalline morphological form is a layer having any of crystalline morphological forms represented by SEM images in FIGS. 7 to 17.

The layer having the morphological form including the hollow elongate body crystals is characterized as follows.

(1) A plurality of elongate bodies (rod-shaped bodies) having independent long axes, wherein the elongate bodies are hollow. The elongate bodies are rod-like in shape.

(2) The elongate bodies having long axes, wherein many of the elongate bodies are polyhedrons of which the section in a plane orthogonal to the long axis is a polygon. Of the elongate body crystals, not less than 50% by volume are elongated polyhedrons. Side surfaces of the polyhedrons are mainly tetrahedron. In some cases, the elongated polyhedron has a plurality of surfaces (grooves) formed at a reentrant angle with a vertex extending in the long axis direction. The reentrant angle here means that at least one of the internal angles of the polygon of the section of the elongate body in a plane orthogonal to the long axis is an angle greater than 180 degrees.

(3) The elongate bodies having the long axes are elongated polyhedrons bodies in many cases. When viewed in a plane orthogonal to the long axis of the elongate body, the section of the elongate body is a polygon, which is observed as a tetragon, a pentagon, or a hexagon.

(4) The plurality of elongate bodies having independent long axes are aligned with their long axes at angles in a predetermined range, preferably in the range of, for example, from 45 degrees to 135 degrees, against the substrate surface. Specifically, for example, the plurality of elongate bodies having independent long axes stand together substantially uniformly on the substrate surface. The region in which the elongate bodies stand together extend in the circumferential direction and the axial direction of the substrate surface and is formed substantially uniformly. The angles of the each independent elongate bodies against the substrate surface may be different each other or the same within the predetermined range.

(5) Each of the elongate bodies having the independent long axes has its one end (proximal) of the length part thereof fixed to the substrate surface.

(6) The morphology of a part near the substrate surface may in some cases be a stack of granular, short rod-shaped, or short curved line-shaped crystals. Some of the elongate bodies having the long axes have their long axes directly or indirectly on the substrate surface. Therefore, in some cases, the elongate bodies having the long axes stand together on the stack.

(7) The length of the elongate bodies having the long axes is, for example, preferably 5 µm to 20 µm, more preferably 9 µm to 11 µm, and further preferably around 10 µm. The diameter of the elongate bodies having the long axes is, for example, preferably 0.01 µm to 5 µm, more preferably 0.05 µm to 4 µm, and further preferably 0.1 µm to 3 µm.

(8) On the surface of the layer including the hollow elongate body crystalline morphological form, there is no other morphological form (for example, an amorphous plate-shaped morphological form) mixed in therewith. In accordance with an exemplary embodiment, for example, not less than 50% by volume, more preferably not less than 70% by volume, of the crystals have the crystalline morphological forms of the aforesaid (1) to (7). Further preferably, substantially all the crystals have the crystalline morphological form of the (7).

(9) In the hollow elongate body crystalline morphological form, other compound or compounds can be present in the coating layer containing the water-insoluble drug constituting the crystals. In that case, the other compound or compounds are present in the state of being distributed into spaces between the plurality of crystals (elongate bodies) of the water-insoluble drug that stand together on the substrate surface of the balloon. As for the proportions of the substances constituting the coating layer, in this case, the proportion (by volume) of the crystals of the water-insoluble drug is by far greater than the proportion of the other compound or compounds.

(10) In the hollow elongate body crystalline morphological form, the water-insoluble drug constituting the crystals exists on the substrate surface of the balloon. In the coating layer on the substrate surface of the balloon that has the water-insoluble drug constituting the crystals, no matrix including the excipient is formed. Therefore, the water-insoluble drug constituting the crystals is not adhered in the matrix substance. The water-insoluble drug constituting the crystals is not embedded in a matrix substance.

(11) In the hollow elongate body crystalline morphological form, the coating layer may contain crystal particles of the water-insoluble drug that are regularly disposed on the substrate surface and excipient particles of an excipient that are irregularly disposed between the crystal particles. In this case, the molecular weight of the excipient is smaller than the molecular weight of the water-insoluble drug. Therefore, the proportion of the excipient particles per a predetermined area of the substrate is smaller than the proportion of the crystal particles, and, accordingly, the excipient particles do not form a matrix. Here, the crystal particles of the water-insoluble drug may be one of the aforesaid elongate bodies, the excipient particles are present in the state of being by far smaller than the crystal particles of the water-insoluble drug and dispersed between the crystal particles of the water-insoluble drug; accordingly, in some cases, the excipient particles may not be observed in an SEM image or a laser microscope image.

The crystal layer of the hollow elongate body morphological form, when delivered into a body as a coating layer formed by coating a substrate surface of a medical device with the drug, is low in toxicity and high in stenosis-inhibition effect. The present inventors consider that the reason for this lies in that the solubility of the drug having a certain crystal morphology after transfer to tissue and the drug's property for being retained in the tissue have influences on these characteristic properties. The water-insoluble drug including the hollow elongate body crystal morphology, upon transfer to the tissue, is reduced in the size of one unit of crystal; therefore, the drug is high in the property for permeation into the tissue. In addition, the water-insoluble drug is high in solubility in the tissue. The high permeation property and high solubility permit the drug to act effectively, whereby stenosis can be inhibited. In addition, the drug is considered to be low in toxicity because the drug is less liable to remain as large lumps in the tissue.

In addition, the layer including the hollow elongate body crystalline morphological form is a morphological form wherein a plurality of substantially uniform elongate bodies having long axes are standing together substantially uniformly and regularly on the substrate surface. Therefore, the size (the length in the long axis direction) of the crystals transferred to the tissue is as small as approximately 10 μm. For this reason, the drug can act uniformly on the lesion affected area, and its property for permeation into the tissue can be enhanced. Further, since the crystals transferred to the tissue are small in size, a situation in which an excess amount of the drug would be retained in the lesion affected area for an excess time is obviated. For this reason, the drug is considered to be able to show a high stenosis-inhibition effect, without exhibiting toxicity.

Where the discharge direction of the dispensing tube 94 is opposite to the rotating direction of the balloon 30, the water-insoluble drug in the coating layer 32 acquires a morphological form including the hollow elongate body crystalline morphological form. The principle of this formation may be considered to lie, for example, in that the coating solution discharged from the opening portion 95 onto the balloon 30 is stimulated by the dispensing tube 94 attendantly on the rotation. In addition, in the state where a part of a side surface on the end portion side of the dispensing tube 94 (a part of the continuous length in the extending direction of the dispensing tube 94) is in contact with the outer surface of the balloon 30, the coating solution is discharged from the opening portion 95 onto the balloon 30. Consequently, suitable contact can be realized between the dispensing tube 94 and the balloon 30, such as to give the morphological form wherein the crystals of the water-insoluble drug include a plurality of elongate bodies having each independent long axis.

In addition, the coating solution is discharged from the opening portion 95 onto the balloon 30, in a region in which the balloon 30 is rotated toward the upper side in the vertical direction. For this reason, the discharge direction of the dispensing tube 94, which extends downward such as to ensure easy discharge of the coating solution, can be relatively easily set to be opposite to the rotating direction of the balloon 30.

If the material constituting the dispensing tube 94 coming into contact with the balloon 30 is polyolefin (fluorine-free polyolefin) such as polyethylene or polypropylene, the dispensing tube 94 is low in organic solvent resistance but is high in affinity for organic solvents and small in contact angles, as compared to a tube made of fluororesin such as PTFE. Accordingly, the coating solution is less liable to be repelled due to the characteristic properties of the material of the dispensing tube 94 at the opening portion 95 and at the part of contact with the balloon 30. Therefore, unevenness is less liable to occur in coating the outer surface of the balloon 30 with the coating solution, and the degree of uniformity of the coating layer can be regulated with high accuracy. Specifically, by using a material having an organic solvent resistance less than that of fluororesin for the dispensing tube 94, it is possible to lower the possibility of unevenness in coating the outer surface of the balloon 30 with the coating solution. In addition, where the material constituting the dispensing tube 94 is polyolefin such as polyethylene or polypropylene, it is also possible to cause unevenness in coating the outer surface of the balloon 30 with the coating solution, by regulating at least one of the moving speed of the dispensing tube 94, the discharge rate of the coating solution, and the rotational speed of the balloon 30. For this reason, by forming the dispensing tube 94 from polyolefin such as polyethylene or polypropylene, the level of the degree of uniformity of the coating layer can be arbitrarily controlled.

In addition, if the material constituting the dispensing tube 94 is fluororesin such as PTFE, ETFE, PFA, and FEP, its affinity for organic solvents is low and contact angles are large. Accordingly, the coating solution is strongly repelled due to the characteristic properties of the material of the dispensing tube 94 at the opening portion 95 and at the part of contact with the balloon 30. Therefore, it is possible to easily cause unevenness (non-uniformity) in coating the outer surface of the balloon 30 with the coating solution. Where the unevenness in coating with the coating solution is heavy, it is possible to increase the amount of the drug actually applied to some parts, while keeping constant the total amount of the drug contained in the coating layer 32 formed on the balloon 30. By this, it is possible to cause the drug to act effectively, without increasing the burden on the living body. The unevenness in coating is preferably a regular non-uniformity and is preferably a stripe pattern (spiral linear body) in which linearly coated parts are aligned in the axial direction X of the balloon 30. By applying the coating solution while rotating the balloon 30 relative to the dispensing tube 94, the coating layer 32 can be easily formed while producing unevenness of coating in a stripe pattern. Note that unevenness of coating is not restricted to the form of a stripe pattern; for example, a state where extremely shaded phases are formed may be adopted.

In the application step, the degree of uniformity of the coating layer 32 can be controlled, for example, by using both a dispensing tube 94 formed of polyolefin and another dispensing tube 94 formed of fluororesin and utilizing the aforementioned different characteristic properties. In the case of using both the dispensing tubes 94 having the different characteristic properties, for example, at the time of sequentially coating balloons 30 of a plurality of balloon catheters 10, a control of changing the dispensing tube 94 according to the balloon 30 can be carried out. In addition, a control of changing the dispensing tube 94 depending on the part being coated of one balloon 30 can also be performed.

The drug in the coating on the outer surface of the balloon 30 can assume different morphological forms such as crystalline form, amorphous form, and mixed forms thereof. In the case where the drug is of the crystalline form, there exist various morphological forms, which differ in crystal structure. Further, crystals and amorphous phases may be disposed regularly in the coating layer 32, or may be disposed irregularly in the coating layer 32.

When the dispensing tube 94 makes contact with the outer surface of the balloon 30, a load acts on the balloon 30. With the balloon 30 rotated in the state where the load is acting on the surface of the balloon 30, a frictional force is generated at the contact part. Then, if the extending direction (discharge direction) toward the opening portion 95 of the dispensing tube 94 is opposite to the rotating direction of the balloon 30, the frictional force is amplified by the rotation of the balloon 30, whereby formation of crystals is induced.

In addition, it is considered that, with the frictional force amplified, a greater stimulus (molecular vibration) is given to the coating solution under the contact of the dispensing tube 94, resulting in an accelerating effect to induce crystalline nucleation. Specifically, for example, with the discharge direction of the dispensing tube 94 set to be opposite to the rotating direction of the balloon 30, the frictional force is amplified, and, accordingly, formation of more crystalline nuclei can be expected.

In addition, where a stimulus of a constant force is given to the coating solution in a continued manner, an effect to form crystalline nuclei of a fixed size can also be expected.

In addition, since the discharge direction of the dispensing tube 94 is opposite to the rotating direction of the balloon 30 and the frictional force is thereby amplified, it can be ensured that even in the case of a balloon 30 having a smooth outer surface such that a frictional force is not easily generated thereon, a frictional force can be generated favorably and formation of crystals can be thereby induced. Therefore, by setting the discharge direction of the dispensing tube 94 opposite to the rotating direction of the balloon 30, it is possible to arbitrarily generate a desirable frictional force in accordance with the material of the balloon 30 and the states of its outer surface, and thereby to form desirable crystals.

In addition, since the balloon 30 is rotated in the direction opposite to the discharge direction of the dispensing tube 94 while a side surface of the dispensing tube 94 is kept in contact with the balloon 30, the coating solution discharged from the discharge end 97 spreads thinly on the smooth balloon 30, so that a coating layer 32 having a uniform thickness can be formed.

Figure 39:
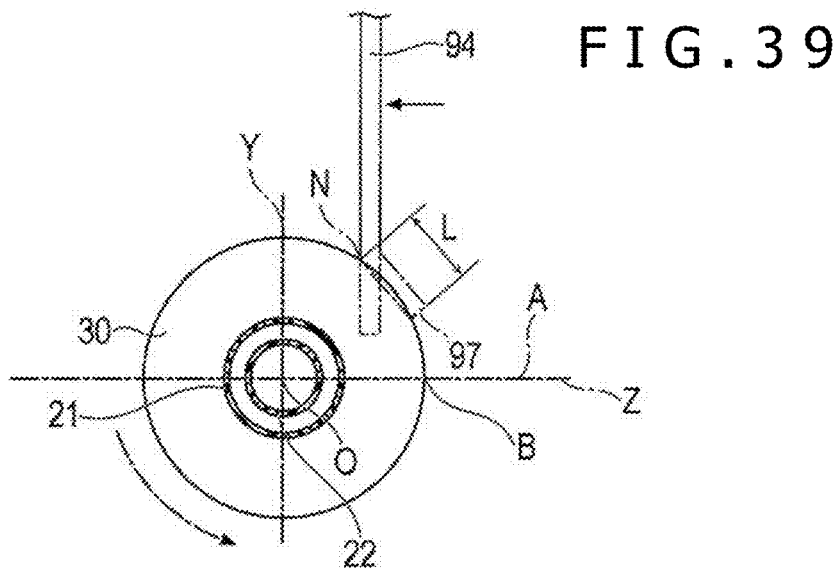
FIG. 39 is a sectional view showing the length of contact of a dispensing tube with a balloon.

Note that the contact length in contact of the dispensing tube 94 with the outer surface of the balloon 30 can be calculated as a theoretical value which is virtually defined as the length L from an intersection N, at which the dispensing tube 94 intersects the outer surface of the balloon 30, to the discharge end 97 of the dispensing tube 94, in the case where the dispensing tube 94 is assumed to be non-flexible, as depicted in FIG. 39. Note that the contact length L as a theoretical value is defined without taking the rotation of the balloon 30 into consideration; thus, the contact length L is a value when the balloon 30 is stationary.

The contact length L in contact of the dispensing tube 94 with the outer surface of the balloon 30 is not particularly limited, and is preferably, for example, 0 mm to 4.0 mm, more preferably 1.0 mm to 4.0 mm. If the contact length L is too large, the frictional force is also increased. In this case, the position of contact of the dispensing tube 94 with the balloon 30 is not maintained, and a distal portion of the dispensing tube 94 is liable to move, in the course of operation, to a position at which the discharge direction coincides with the rotating direction of the balloon 30.

In addition, the load exerted on the balloon 30 by the dispensing tube 94 is preferably, for example, 0 mN to 158 mN, more preferably 1 mN to 158 mN. If the load on the balloon 30 is too high, the frictional force is also increased. In this case, the position of contact of the dispensing tube 94 with the balloon 30 is not maintained, and the distal portion of the dispensing tube 94 is liable to move, in the course of operation, to a position at which the discharge direction coincides with the rotating direction of the balloon 30.

Then, the dispensing tube 94 is gradually moved in the axial direction X while the balloon 30 is rotated, whereby the coating layer 32 is formed on the outer surface of the balloon 30 gradually along the axial direction X. After the range of the part to be coated of the balloon 30 is entirely formed thereon with the coating layer 32, the rotation mechanism portion 60, the movement mechanism portion 80, and the application mechanism portion 90 are stopped.

Thereafter, the balloon catheter 10 is detached from the balloon coating apparatus 50, whereby coating of the balloon 30 is completed.

As has been described above, in the balloon coating method according to the present embodiment, the coating solution is discharged while the dispensing tube 94 is kept in contact with the outer surface of the balloon 30 in such a manner that the opening portion 95 is oriented in the direction opposite to the rotating direction of the balloon 30. Therefore, the water-insoluble drug in the coating layer 32 formed on the outer surface of the balloon 30 can be formed in a morphological form wherein the crystals include a plurality of elongate bodies having each independent long axes. The plurality of elongate bodies may extend substantially outward in a circumferential direction with respect to the balloon surface, or may be arranged in a direction substantially parallel to the circumferential direction. The plurality of elongate bodies may be arranged in a fixed direction, or may be arranged randomly in a plurality of directions. The plurality of elongate bodies may be present in the state of being combined with one another, or may be present in contact with one another in a state wherein the plurality of adjacent elongate bodies form different angles with one another. The plurality of elongate bodies are formed in such a manner that the crystals do not include a structure wherein the crystals, instead of assuming elongated-body shapes, are fused together during/or after the process of formation of the plurality of elongate bodies and, hence, do not show the elongated-body profile any more (for example, a structure wherein the crystals extend in a flat form on the balloon surface). The balloon coating method according to the present embodiment helps enable such coating that a region in which drug crystals (a plurality of elongate bodies) are absent is not formed on the balloon surface (such coating that the drug crystals are formed throughout the coated region). Alternatively, the balloon coating method according to the present embodiment ensures that regions in which drug crystals (a plurality of elongate bodies) are absent and regions in which the drug crystals are present can be formed, regularly or irregularly, on the balloon surface. In addition, according to the aforesaid balloon coating method, the coating solution is discharged while the dispensing tube 94 is kept in contact with the outer surface of the balloon 30 in such a manner that the opening portion 95 is oriented in the direction opposite to the rotating direction of the balloon 30, whereby suitable contact can be given between the dispensing tube 94 and the balloon 30, and the morphological form and the size of the drug contained in the coating layer 32 can be freely set.

In addition, since the coating solution is discharged in a state where a continuous length (a length which is continuous in the extending direction of the dispensing tube 94) of a side surface on the end portion side where the opening portion 95 is formed, of the dispensing tube 94, is kept in contact with the outer surface of the balloon 30, suitable contact can be realized between the dispensing tube 94 and the balloon 30 in such a manner that the crystals of the water-insoluble drug assume a morphological form which can include a plurality of elongate bodies having each independent long axes.

In addition, in the application step, the flexible dispensing tube 94 is pressed against the outer surface of the balloon 30 while being bent, and the coating solution is discharged, which can help ensure that, even if the balloon 30 becomes eccentric, damaging of the balloon 30 can be restrained, since the dispensing tube 94 moves following up to the balloon 30. In addition, favorable contact of the dispensing tube 94 with the balloon 30 can be maintained. Accordingly, the thickness and the morphological form of the coating layer 32 to be formed can be set with relatively high accuracy.

In addition, in the application step, the coating solution is discharged from the opening portion 95 while the dispensing tube 94 is kept in contact with a part at which the balloon 30 is rotated toward the vertically upper side, which helps enable the dispensing tube 94 to be easily disposed in such a manner that the opening portion 95 is oriented in the direction opposite to the rotating direction of the balloon 30.

In addition, where the water-insoluble drug is rapamycin, paclitaxel, docetaxel, or everolimus, restenosis of a stenosed part in a blood vessel can be favorably inhibited by the aforementioned water-insoluble drug the crystals of which are formed in a morphological form including a plurality of elongate bodies having each independent long axes.

In addition, in the balloon coating method according to the present embodiment, the dispensing tube 94 formed from polyolefin makes contact with the balloon 30. As a result, the affinity of the dispensing tube 94 for organic solvents is high and the contact angles are small, as compared to the case of using a fluororesin-made tube, and the coating solution is less liable to be repelled at the opening portion 95 of the dispensing tube 94 or at the part of contact with the balloon 30. Therefore, uneven coating of the outer surface of the balloon 30 with the coating solution is less liable to occur, and the degree of uniformity of the coating layer 32 can be regulated with relatively high accuracy. Further, since the degree of uniformity of the coating layer 32 can be regulated with relative high accuracy, the morphological form and the size of the drug contained in the coating layer 32 can be freely set.

In addition, where the dispensing tube 94 is formed from polyethylene or polypropylene, affinity of the dispensing tube 94 for organic solvents can be securely enhanced and the contact angles can be assuredly reduced, as compared to the case of a fluororesin-made tube. Consequently, the coating solution is less liable to be repelled at the opening portion 95 of the dispensing tube 94 or at the part of contact with the balloon 30.

In addition, in the application step, the degree of uniformity of the coating layer 32 may be controlled by using the dispensing tube 94 formed of a polyolefin or another dispensing tube 94 formed of a fluororesin. In this case, while the degree of uniformity of the coating layer 32 is enhanced by use of the dispensing tube 94 formed of the polyolefin, unevenness of coating can be imparted to the coating layer 32 by use of the other dispensing tube 94 formed of the fluororesin, and, consequently, the level of the degree of uniformity of the coating layer 32 can be controlled arbitrarily.

In addition, in the application step, the degree of uniformity (evenness) of the coating layer 32 may be controlled by regulating at least one of the moving speed of the dispensing tube 94 relative to the balloon 30 in the axial direction X, the discharge rate of the coating solution from the dispensing tube 94, and the rotating speed of the balloon 30. In this case, the level of the degree of uniformity of the coating layer 32 can be controlled arbitrarily.

In addition, in the balloon coating method according to the present embodiment, the dispensing tube 94 coming into contact with the balloon 30 may be formed from a fluororesin. In this case, affinity of the dispensing tube 94 for solvent is lowered and the contact angle is enlarged, so that the coating solution is strongly repelled at the opening portion 95 and at the part of contact with the balloon 30. As a result, uneven coating of the outer surface of the balloon 30 with the coating solution can be easily effected, and the morphological form and the size of the drug contained in the coating layer 32 can be freely set. In addition, where the unevenness in coating with the coating solution is heavy, the amount of the drug actually applied to some parts can be increased, while keeping constant the total amount of the drug coated to the balloon 30. By this, it is possible to cause the drug to act effectively, without increasing the burden on the living body.

In addition, in the application step, the coating solution may be applied while rotating the balloon 30 relative to the dispensing tube 94, whereby a coating layer 32 showing unevenness of coating can be easily formed while forming a stripe pattern on the outer surface of the balloon 30 from the coating solution.

In addition, in the positioning method for balloon coating in the present embodiment, the part where the opening portion 95 is formed, of the dispensing tube 94, is brought into contact with the outer surface of the balloon 30 by moving the dispensing tube 94 in a direction intersecting the extending direction of the dispensing tube 94. Therefore, the burden on the balloon 30 can be reduced, as compared to the case where the dispensing tube 94 is moved in its extending direction to make contact with the balloon 30 in the manner of colliding against the balloon 30. Consequently, the dispensing tube 94 and the balloon 30 contact each other in a suitable state, so that the morphological form and the size of the water-insoluble drug contained in the coating layer 32 can be freely set. In addition, with the burden on the balloon 30 reduced, it is unnecessary to provide an operating step for checking whether or not the balloon 30 has been deformed or damaged. Consequently, workability is relatively enhanced.

In addition, the positioning method for balloon coating may further include an application step of discharging the coating solution from the opening portion 95 to apply the coating solution to the outer surface of the balloon 30 while moving the dispensing tube 94 relative to the balloon 30 in the axial direction of the balloon 30. In this case, the coating solution can be applied to the balloon 30, which is inhibited from being deformed or damaged in the positioning step. Therefore, the quantity, thickness and the like of the coating solution applied to the balloon 30 can be set with relatively high accuracy. Consequently, the morphological form and size of the drug contained in the coating layer 32 formed can be freely set.

In addition, in the positioning step, that part of the dispensing tube 94 at which the opening portion 95 for discharging the coating solution is formed may be brought into contact with the outer surface of the balloon 30, by moving the dispensing tube 94 in a direction intersecting the extending direction of the dispensing tube 94, after moving the dispensing tube 94 in the extending direction of the dispensing tube 94 without making the dispensing tube 94 contact the balloon 30. In this case, the dispensing tube 94 does not contact the balloon 30 at the time of moving the dispensing tube 94 in the extending direction thereof. Therefore, the burden on the balloon 30 is reduced, and it is unnecessary to provide an operating step for checking whether or not the balloon 30 has been deformed or damaged. Thus, workability is relatively enhanced.

In addition, in the contact step, the dispensing tube 94 may be positioned relative to the balloon 30 in such a manner that the virtual position V at which the opening portion 95 would be located if the dispensing tube 94 is assumed to be non-flexible is located at a position deviated from the reference plane A toward the rotating direction side of the balloon 30 by an angle, for example, within the range of 0 degrees to 40 degrees, with the axis of the balloon 30 as the vertex of the angle, in a region extending from the reference plane A in a direction opposite to the discharge direction of the dispensing tube 94. In this case, the dispensing tube 94 can be inhibited from slipping off from the contact position due to a frictional force between the dispensing tube 94 and the balloon 30, and favorable contact is maintained. Consequently, the morphological form and size of the water-insoluble drug contained in the coating layer 32 can be freely set.

In addition, in the balloon coating method according to the present embodiment, that part of the dispensing tube 94 at which the opening portion 95 is formed (a side surface of the distal of the dispensing tube 94) may be brought into contact with the outer surface of the balloon 30 by moving the dispensing tube 94 in a direction intersecting the extending direction of the dispensing tube 94. By this, the dispensing tube 94 can be inhibited from slipping off from the contact position due to a frictional force between the dispensing tube 94 and the balloon 30, and favorable contact is maintained. Accordingly, the morphological form and size of the water-insoluble drug contained in the coating layer 32 can be freely set.

Note that the present disclosure is not to be limited only to the aforementioned embodiment, and various modifications can be made by a person skilled in the art within the technical thought of the present disclosure. For instance, while application of the coating solution is conducted along the direction from the distal side toward the proximal side of the balloon 30 in the aforementioned embodiment, the application may be carried out along the direction from the proximal side toward the distal side.

In addition, while the dispensing tube 94 extends downward along the vertical direction to make contact with the balloon 30 in the present embodiment, the extending direction of the dispensing tube 94 is not specifically restricted. For example, the extending direction may be inclined against the vertical direction, or the dispensing tube 94 may extend toward a lateral side or an upper side.

In addition, while the outer circumferential surface of the balloon 30 is circular in shape in section orthogonal to the axis in the present embodiment, it may not be circular. The balloon coating method according to the present embodiment helps ensure that, even if the outer circumferential surface of the balloon is not circular in the shape, the dispensing tube 94 can move following up to the shape of the balloon, so that the coating solution can be applied uniformly while inhibiting unevenness of coating, and the desired coating layer 32 can be suitably formed.

In addition, while coating is applied to the balloon 30 of the balloon catheter 10 of the over-the-wire type in the balloon coating method according to the aforementioned embodiment, the coating may be applied to a balloon of a balloon catheter of the rapid exchange type wherein a guide wire lumen is only formed in a distal portion of a catheter.

EXAMPLES

The present disclosure will now be described below by showing Examples and Comparative Examples, but the disclosure is not limited to the following Examples.

Test 1 (Verification Test Concerning Rotating Direction of Balloon) Production of Drug Eluting Balloon

Example 1

(1) Preparation of Coating Solution 1

56 mg of L-serine ethyl ester hydrochloride (CAS No. 26348-61-8) and 134.4 mg of paclitaxel (CAS No. 33069-62-4) were weighed. To these compounds were added 1.2 mL of anhydrous ethanol, 1.6 mL of tetrahydrofuran, and 0.4 mL of RO (Reverse Osmosis film)-treated water (hereinafter referred to as RO water), to dissolve the compounds, thereby preparing a coating solution 1.

(2) Coating of Balloon with Drug

A balloon catheter (made by Terumo Corporation; the balloon (expandable portion) was formed from nylon elastomer) measuring 3.0 mm in diameter and 20 mm in length (expandable portion) when expanded was provided. The coating solution 1 was applied to the balloon in an expanded state, in such a manner that the solvent of the coating solution was volatilized slowly and that the amount of paclitaxel in the coating would be approximately 3 µg/mm$^2$.

Specifically, a dispensing tube having an opening portion at a distalmost portion (the dispensing tube was formed from polyethylene) was moved toward the balloon catheter from a lateral direction (horizontal direction), and was disposed such that part of a side surface of the distal of the dispensing tube was set along and in contact with the outer surface of the balloon. In this instance, the dispensing tube was positioned such that the virtual position in regard of the dispensing tube is within an angular range of 0 degrees to 40 degrees from the reference plane of the balloon (a horizontal plane passing through the axis of the balloon) toward the rotating direction side. Then, while keeping the side surface of the distal of the dispensing tube in contact with the outer surface of the balloon, the drug was discharged from the distal opening portion of the dispensing tube. In this state, the balloon catheter was rotated about the axis of the balloon, in the direction opposite (reverse) to the drug discharge direction. By regulating the moving speed of the dispensing tube in the axial direction of the balloon and the rotating speed of the balloon, the drug was discharged, upon the start of rotation, at a rate of 0.053 µL/second during coating. Thereafter, the thus coated balloon was dried, to produce a drug eluting balloon.

Example 2

(1) Preparation of Coating Solution 2

70 mg of L-serine ethyl ester hydrochloride and 180 mg of paclitaxel were weighed. To these compounds were added 1.5 mL of anhydrous ethanol, 2.0 mL of acetone, 0.5 mL of tetrahydrofuran, and 1 mL of RO water, to dissolve the compounds, thereby preparing a coating solution 2.

(2) Coating of Balloon with Drug

A balloon catheter (made by Terumo Corporation; the balloon (expandable portion) was formed from nylon elastomer) measuring 3.0 mm in diameter and 20 mm in length (expandable portion) when expanded was provided. The coating solution 2 was applied to the balloon in an expanded state, in such a manner that the solvent of the coating solution was volatilized slowly and that the amount of paclitaxel in the coating would be approximately 3 µg/mm$^2$.

Specifically, coating was conducted in the same manner as the method described in Example 1, except that the drug was discharged at a rate of 0.088 µL/second. Thereafter, the thus coated balloon was dried, to produce a drug eluting balloon.

Example 3

(1) Preparation of Coating Solution 3

70 mg of L-serine ethyl ester hydrochloride and 168 mg of paclitaxel were weighed. To these compounds were added 1.5 mL of anhydrous ethanol, 1.5 mL of tetrahydrofuran, and 1 mL of RO water, to dissolve the compounds, thereby preparing a coating solution 3.

(2) Coating of Balloon with Drug

A balloon catheter (made by Terumo Corporation; the balloon (expandable portion) was formed from nylon elastomer) measuring 3.0 mm in diameter and 20 mm in length (expandable portion) when expanded was provided. The coating solution 3 was applied to the balloon in an expanded state, in such a manner that the solvent of the coating solution 3 was volatilized slowly and that the amount of paclitaxel in the coating would be approximately 3 µg/mm$^2$.

Specifically, coating was conducted in the same manner as the method described in Example 1, except that the drug was discharged at a rate of 0.101 µL/second. Thereafter, the thus coated balloon was dried, to produce a drug eluting balloon.

Example 4

(1) Preparation of Coating Solution 4

70 mg of L-serine ethyl ester hydrochloride and 180 mg of paclitaxel were weighed. To these compounds were added 1.75 mL of anhydrous ethanol, 1.5 mL of tetrahydrofuran, and 0.75 mL of RO water, to dissolve the compounds, thereby preparing a coating solution 4.

(2) Coating of Balloon with Drug

A balloon catheter (made by Terumo Corporation; the balloon (expandable portion) was formed from nylon elastomer) measuring 3.0 mm in diameter and 20 mm in length (expandable portion) when expanded was provided. The coating solution 4 was applied to the balloon in an expanded state, in such a manner that the solvent of the coating solution was volatilized slowly and that the amount of paclitaxel in the coating would be approximately 3 µg/mm$^2$.

Specifically, coating was performed in the same manner as the method described in Example 1, except that the drug was discharged at a rate of 0.092 µL/second. Thereafter, the thus coated balloon was dried, to produce a drug eluting balloon.

(1) Preparation of Coating Solution 5

37.8 mg of L-aspartate dimethyl ester hydrochloride (CAS No. 32213-95-9) and 81 mg of paclitaxel were weighed. To these compounds were added 0.75 mL of anhydrous ethanol, 0.96 mL of tetrahydrofuran, and 0.27 mL of RO water, to dissolve the compounds, thereby preparing a coating solution 5.

(2) Coating of Balloon with Drug

A balloon catheter (made by Terumo Corporation; the balloon (expandable portion) was formed from nylon elastomer) measuring 3.0 mm in diameter and 20 mm in length (expandable portion) when expanded was provided. The coating solution 5 was applied to the balloon in an expanded state, in such a manner that the solvent of the coating solution was volatilized slowly and that the amount of paclitaxel in the coating would be approximately 3 µg/mm$^2$.

Specifically, coating was conducted in the same manner as the method described in Example 1, except that the drug was discharged at a rate of 0.055 µL/second. Thereafter, the thus coated balloon was dried, to produce a drug eluting balloon.

Example 6

(1) Preparation of Coating Solution 6

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 6.

(2) Coating of Balloon with Drug

A balloon catheter (made by Terumo Corporation; the balloon (expandable portion) was formed from nylon elastomer) measuring 3.0 mm in diameter and 20 mm in length (expandable portion) when expanded was provided. The coating solution 6 was applied to the balloon in an expanded state, in such a manner that the solvent of the coating solution was volatilized slowly and that the amount of paclitaxel in the coating would be approximately 3 µg/mm$^2$.

Specifically, coating was performed in the same manner as the method described in Example 1, except that the drug was discharged at a rate of 0.101 µL/second. Thereafter, the thus coated balloon was dried, to produce a drug eluting balloon.

Comparative Example 1

(1) Preparation of Coating Solution 7

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 6.

(2) Coating of Balloon with Drug

A balloon catheter (made by Terumo Corporation; the balloon (expandable portion) was formed from nylon elastomer) measuring 3.0 mm in diameter and 20 mm in length (expandable portion) when expanded was provided. The coating solution 7 was applied to the balloon in an expanded state, in such a manner that the solvent of the coating solution was volatilized slowly and that the amount of paclitaxel in the coating would be approximately 3 µg/mm$^2$.

Specifically, coating was conducted in the same manner as the method described in Example 1, except that the drug was discharged at a rate of 0.101 µL/second and the balloon catheter was rotated about the long axis in the direction coincident with the drug discharge direction. Thereafter, the thus coated balloon was dried, to produce a drug eluting balloon.

Scanning Electron Microscope Observation (SEM) of Coating Layer of Drug Eluting Balloon With respect to the drug eluting balloons of Examples 1 to 6 (FIGS. 7 to 17) and Comparative Example 1 (FIG. 18), the drug eluting balloon after drying was cut to an appropriate size, the cut piece was placed on a support base, and platinum was vapor deposited thereon from above. With respect to the samples obtained upon platinum vapor deposition, the surface and the inside of the coating layer were observed under a scanning electron microscope (SEM).

Results of Test 1

For the coating layers of Examples 1 to 6 wherein the discharge direction was opposite to the rotating direction, it was seen from the SEM pictures that a crystal layer of a morphological form of hollow elongate bodies projecting (in inverted state) outward in the circumferential direction with reference to the balloon surface was observed.

In Examples 1 to 6, as shown in FIGS. 7 to 17, it was observed that a coating layer including a morphological form of hollow elongate bodies was formed, and uniform paclitaxel crystals in the form of hollow elongate bodies approximately 10 µm in length were evenly formed on the outer surface of the balloon. The paclitaxel crystals in the form of hollow elongate bodies had long axes, and the elongate bodies (approximately 10 µm) having the long axes were formed to be substantially perpendicular to the outer surface of the balloon. The diameter of the elongate bodies was approximately 2 µm. In addition, the sections of the elongate bodies in a plane orthogonal to the long axis were polygonal in shape. The polygons here had, for example, tetragons. Further, these substantially uniform hollow elongate body-shaped crystals of paclitaxel were formed in the same morphological form (structure and shape), evenly and densely (in substantially the same density) throughout the outer surface of the balloon.

Figure 18:
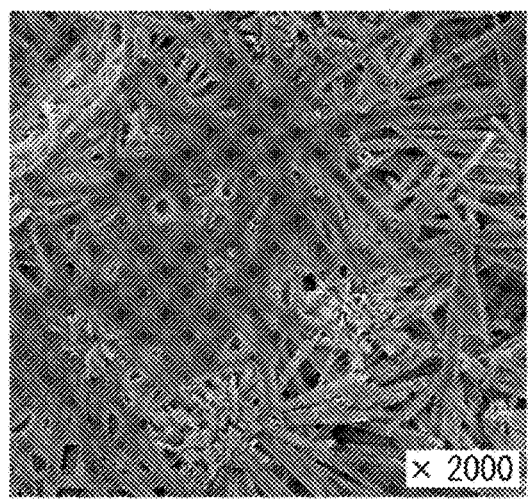
FIG. 18 is a view showing an SEM image (2,000 times) of crystals observed at a substrate surface of a coating layer produced in Comparative Example 1.

Specifically, for example, in Comparative Example 1 wherein the discharge direction was coincident with the rotating direction, amorphous phases and crystals were mixedly present in the same plane, as seen in the SEM picture shown in FIG. 18.

Test 2 (Verification Test Concerning Constituent Material of Balloon) Production of Drug Eluting Balloon

Example 7

(1) Preparation of Coating Solution 8

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 8.

(2) Coating of Balloon with Drug

A balloon catheter (made by Kaneka Corporation; the balloon (expandable portion) was formed from nylon elastomer) measuring 7.0 mm in diameter and 200 mm in length (expandable portion) when expanded was provided. The coating solution 8 was applied to the balloon in an expanded state, in such a manner that the solvent of the coating solution was volatilized slowly and that the amount of paclitaxel in the coating would be approximately 3 µg/mm$^2$.

Specifically, a dispensing tube (outside diameter, 0.61 mm; inside diameter, 0.28 mm; the dispensing tube was formed from polyethylene) having an opening portion at a distalmost portion was moved toward the balloon catheter from a lateral direction (horizontal direction), and was disposed such that part of a side surface of the distal of the dispensing tube was set along and in contact with the outer surface of the balloon. While keeping the side surface of the distal of the dispensing tube in contact with the outer surface of the balloon, the drug was discharged from the distal opening portion of the dispensing tube. In this state, the balloon catheter was rotated about the axis of the balloon in the direction opposite (reverse) to the drug discharge direction. By regulating the moving speed of the dispensing tube in the axial direction of the balloon and the rotating speed of the balloon, the drug was discharged, upon the start of rotation, at a rate of 0.378 µL/second during coating. Thereafter, the thus coated balloon was dried, to produce a drug eluting balloon.

Example 8

(1) Preparation of Coating Solution 9

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 9.

(2) Coating of Balloon with Drug

A balloon catheter (made by Kaneka Corporation; the balloon (expandable portion) was formed from nylon elastomer) measuring 4.0 mm in diameter and 200 mm in length (expandable portion) when expanded was provided. The coating solution 9 was applied to the balloon in an expanded state, in such a manner that the solvent of the coating solution was volatilized slowly and that the amount of paclitaxel in the coating would be approximately 3 µg/mm$^2$.

Specifically, coating was conducted in the same manner as the method described in Example 7, except that the drug was discharged by a dispensing tube (outside diameter, 0.99 mm; inside diameter, 0.61 mm; the dispensing tube was formed from polypropylene) at a rate of 0.191 µL/second. Thereafter, the thus coated balloon was dried, to produce a drug eluting balloon.

Example 9

A drug eluting balloon was produced under the same conditions as in Example 8, except that the drug discharge rate was 0.240 µL/second.

Comparative Example 2

(1) Preparation of Coating Solution 10

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 10.

(2) Coating of Balloon with Drug

A balloon catheter (made by Kaneka Corporation; the balloon (expandable portion) was formed from PTFE) measuring 7.0 mm in diameter and 200 mm in length (expandable portion) when expanded was provided. The coating solution 10 was applied to the balloon in an expanded state, in such a manner that the solvent of the coating solution was volatilized slowly and that the amount of paclitaxel in the coating would be approximately 3 µg/mm$^2$.

Specifically, coating was performed in the same manner as the method described in Example 7, except that the drug was discharged by a dispensing tube (outside diameter, 0.60 mm; inside diameter, 0.30 mm; the dispensing tube was formed from PTFE) at a rate of 0.335 µL/second. Thereafter, the thus coated balloon was dried, to produce a drug eluting balloon.

Comparative Example 3

(1) Preparation of Coating Solution 11

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 11.

(2) Coating of Balloon with Drug

A balloon catheter (made by Kaneka Corporation; the balloon (expandable portion) was formed from nylon elastomer) measuring 4.0 mm in diameter and 200 mm in length (expandable portion) when expanded was provided. The coating solution 11 was applied to the balloon in an expanded state, in such a manner that the solvent of the coating solution was volatilized slowly and that the amount of paclitaxel in the coating would be approximately 3 µg/mm$^2$.

Specifically, coating was conducted in the same manner as the method described in Example 7, except that the drug was discharged by a dispensing tube (outside diameter, 0.304 mm; inside diameter, 0.152 mm; the dispensing tube was formed from PTFE) at a rate of 0.145 µL/second and the balloon catheter was rotated about the axis of the balloon in the direction coincident with the drug discharge direction. Thereafter, the thus coated balloon was dried, to produce a drug eluting balloon.

Comparative Example 4

(1) Preparation of Coating Solution 12

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 12.

(2) Coating of Balloon with Drug

A balloon catheter (made by Kaneka Corporation; the balloon (expandable portion) was formed from nylon elastomer) measuring 7.0 mm in diameter and 200 mm in length (expandable portion) when expanded was provided. The coating solution 12 was applied to the balloon in an expanded state, in such a manner that the solvent of the coating solution was volatilized slowly and that the amount of paclitaxel in the coating would be approximately 3 µg/mm$^2$.

Specifically, coating was performed in the same manner as the method described in Example 7, except that the drug was discharged by a dispensing tube (outside diameter, 0.90 mm; inside diameter, 0.51 mm; the dispensing tube was formed from All-Teflon (registered trademark)) at a rate of 0.378 µL/second. Thereafter, the thus coated balloon was dried, to produce a drug eluting balloon.

Laser Microscope Observation of Drug Coating Layer of Drug Eluting Balloon

In regard of the drug eluting balloons of Examples 7 to 9 (FIGS. 19 to 24) and Comparative Examples 2 to 4 (FIGS. 25 to 30), the surface was photographed, and the surface of the coating layer was observed under a laser microscope.
Results of Test 2

In Example 7 wherein dispensing tube formed of a (non-fluorine-containing) polyolefin (polyethylene or polypropylene) was used as constituent material, it was observed that the coating layer covers the balloon uniformly without any unevenness, and the balloon was non-exposed over substantially the whole surface area.

Figure 19:
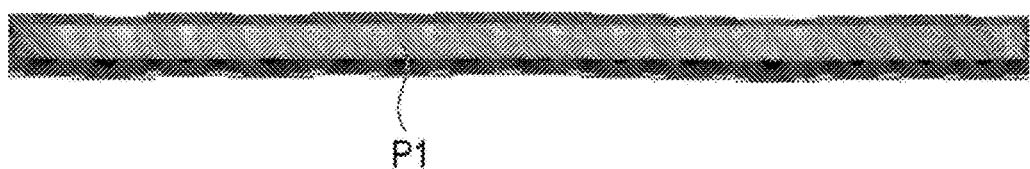
FIG. 19 is a view showing a picture obtained by photographing a surface of a balloon produced in Example 7.
Figure 20:
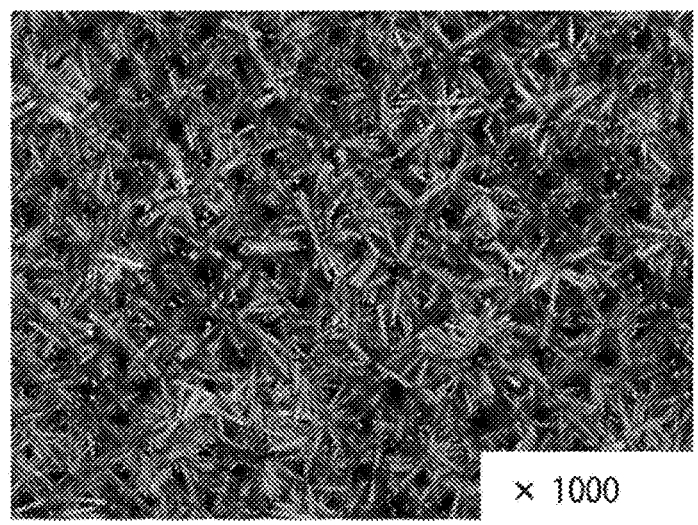
FIG. 20 is a view showing a laser microscope image (1,000 times) of crystals observed at a substrate surface of a coating layer at a central portion P1 of the balloon shown in FIG. 19.
Figure 21:
FIG. 21 is a view showing a picture obtained by photographing a surface of a balloon produced in Example 8.
Figure 22:
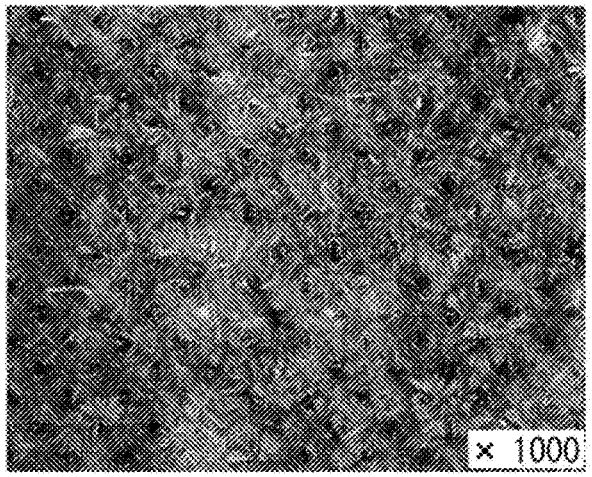
FIG. 22 is a view showing a laser microscope image (1,000 times) of crystals observed at a substrate surface of a coating layer at a central portion P2 of the balloon shown in FIG. 21.

In Examples 7 and 8, as seen in the pictures shown in FIGS. 19 and 21, the coating layer was observed to be coating the outer surface of the balloon uniformly without any unevenness over the area ranging from a distal portion to a proximal portion. In addition, from FIG. 20 showing a laser microscope image of a central portion P1 of the balloon of Example 7 and FIG. 22 showing a laser microscope image of a central portion P2 of the balloon of Example 8, it was observed that the water-insoluble drug in the coating layer on the balloon is formed in a morphological form including hollow elongate body crystals.

Figure 23:
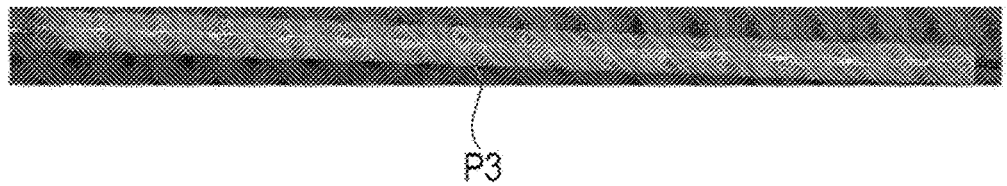
FIG. 23 is a view showing a picture obtained by photographing a surface of a balloon produced in Example 9.
Figure 24:
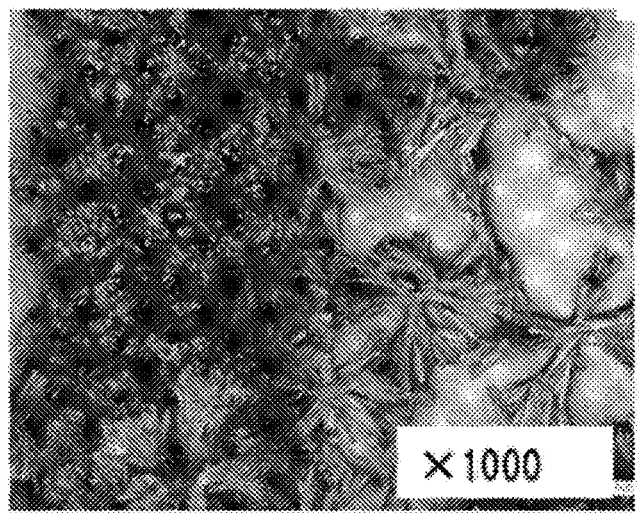
FIG. 24 is a view showing a laser microscope image (1,000 times) of crystals observed at a substrate surface of a coating layer at a central portion P3 of the balloon shown in FIG. 23.
Figure 25:
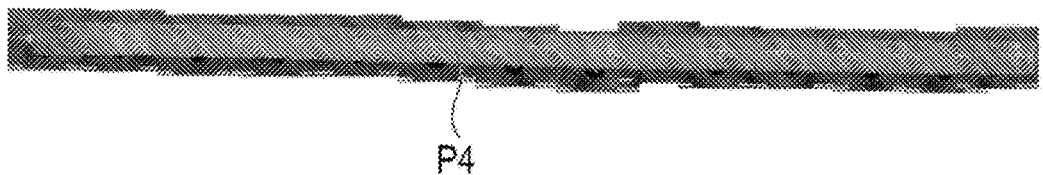
FIG. 25 is a view showing a picture obtained by photographing a surface of a balloon produced in Comparative Example 2.

In addition, in Example 9 wherein the constituent material of the dispensing tube is a polyolefin (polypropylene), it was observed, from the picture shown in FIG. 23 and from FIG. 24 showing a laser microscope image of a central portion P3 of the balloon, that a non-uniform coating layer such that the outer surface of the balloon is partly exposed was formed, by only changing the discharge rate as compared to Example 8. As a result, it was confirmed that when the constituent material of the dispensing tube is a polyolefin (polypropylene), the coating layer on the outer surface of the balloon could not only be formed in a uniform state but also be formed in a non-uniform state.

Figure 26:
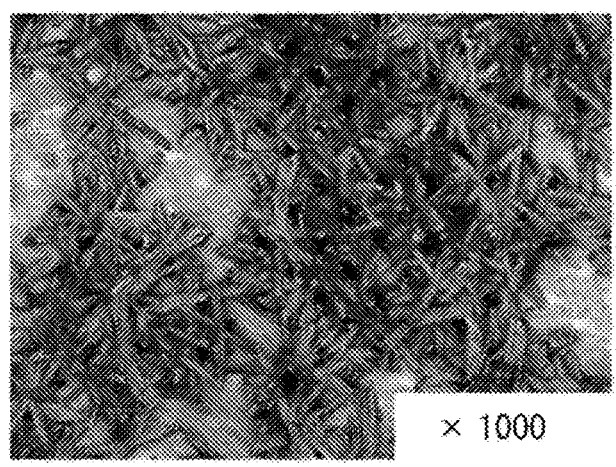
FIG. 26 is a view showing a laser microscope image (1,000 times) of crystals observed at a substrate surface of a coating layer at a central portion P4 of the balloon shown in FIG. 25.
Figure 27:
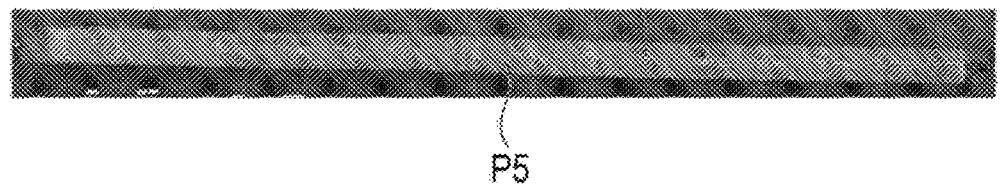
FIG. 27 is a view showing a picture obtained by photographing a surface of a balloon produced in Comparative Example 3.
Figure 28:
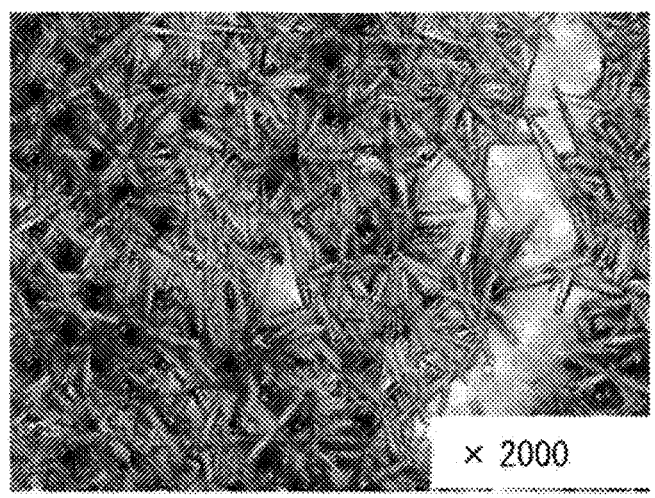
FIG. 28 is a view showing a laser microscope image (2,000 times) of crystals observed at a substrate surface of a coating layer at a central portion P5 of the balloon shown in FIG. 27.
Figure 29:
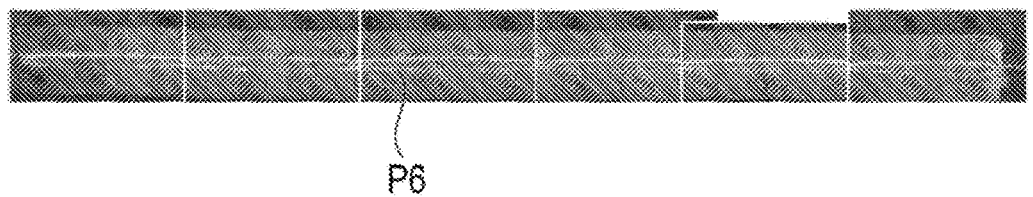
FIG. 29 is a view showing a picture obtained by photographing a surface of a balloon produced in Comparative Example 4.
Figure 30:
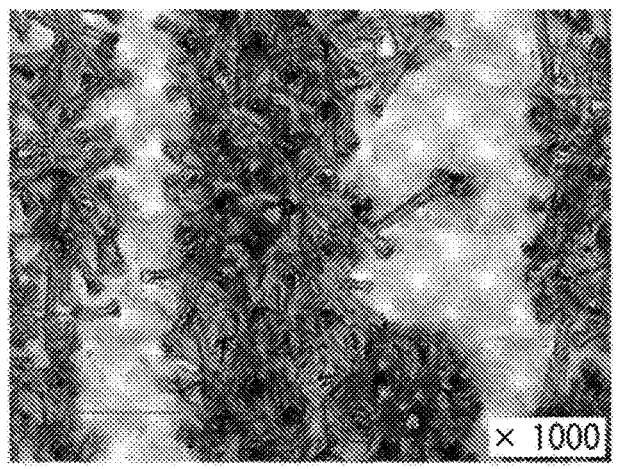
FIG. 30 is a view showing a laser microscope image (1,000 times) of crystals observed at a substrate surface of a coating layer at a central portion P6 of the balloon shown in FIG. 29.
Figure 36A:
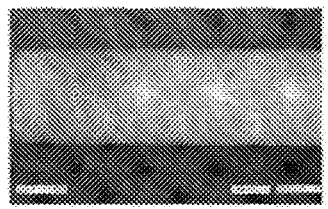
Figure 36B:
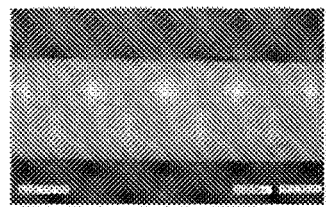
Figure 36C:
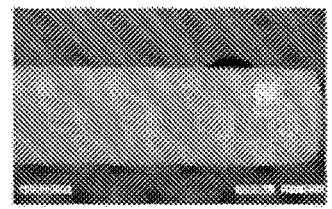
Figure 37A:
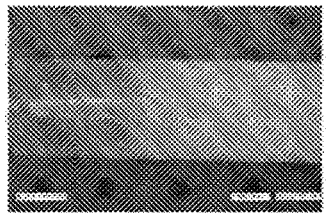
Figure 37B:
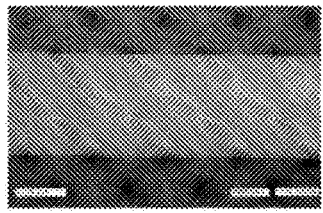
Figure 37C:
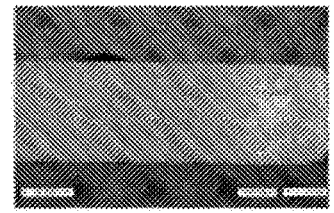

Specifically, for example, in Comparative Examples 2 to 4 wherein the constituent material is a fluororesin, as shown in FIGS. 25 to 30, the coating layer was non-uniformly coated with much unevenness of coating, and parts where the balloon was exposed were observed, in the area ranging from a distal portion to a proximal portion of the outer surface of the balloon. The unevenness of coating was formed in a stripe pattern such that the coating layers are aligned along the axial direction of the balloon. From FIG. 26 showing a laser microscope image of a central portion P4 of the balloon of Comparative Example 2, FIG. 28 showing a laser microscope image of a central portion P5 of the balloon of Comparative Example 3, and FIG. 30 showing a laser microscope image of a central portion P6 of the balloon of Comparative Example 4, it was observed that the crystals of the water-insoluble drug in the coating layer were mostly formed in the manner of lying along the surface of the balloon.

Test 3 (Verification Test Concerning Contact Position Between Dispensing Tube and Balloon)
Production of Drug Eluting Balloon Example 10

(1) Preparation of Coating Solution 13

140 mg of L-serine ethyl ester hydrochloride and 336 mg of paclitaxel were weighed. To these compounds were added 3.0 mL of anhydrous ethanol, 4.0 mL of acetone, 1.0 mL of tetrahydrofuran, and 2 mL of RO water, to dissolve the compounds, thereby preparing a coating solution 13.

(2) Coating of Balloon with Drug

A balloon catheter (made by Kaneka Corporation; the balloon (expandable portion) was formed from nylon elastomer) measuring 7.0 mm in diameter and 200 mm in length (expandable portion) when expanded was provided. The coating solution 13 was applied to the balloon in an expanded state, in such a manner that the solvent of the coating solution was volatilized slowly and that the amount of paclitaxel in the coating would be approximately 3 µg/mm$^2$.

Specifically, a dispensing tube (outside diameter, 0.61 mm; inside diameter, 0.28 mm; length, 6 mm; the dispensing tube was formed from polyethylene) having an opening portion at a distalmost portion was put in contact with a reference position (deviated from the reference plane toward the balloon rotating direction side by an angle of 0 degrees) of the outer surface of the balloon in a non-bending manner, and this position was made to be the drug-discharging position without moving the dispensing tube in the vertical direction (Y-axis direction) or a horizontal direction (Z-axis direction). The virtual position of the distal portion of the dispensing tube in this case was located at a position deviated from the reference plane toward the balloon rotating direction side by an angle of 0 degrees, with the axis of the balloon as the vertex of the angle. Thereafter, while keeping a side surface of the distal of the dispensing tube in contact with the outer surface of the balloon, the drug was discharged from the distal opening portion of the dispensing tube. In this state, the balloon catheter was rotated about the axis of the balloon in the direction opposite (reverse) to the drug discharge direction. By regulating the moving speed of the dispensing tube in the axial direction of the balloon and the rotating speed of the balloon, the drug was discharged, upon the start of rotation, at a rate of 0.378 µL/second during coating. Thereafter, the thus coated balloon was dried, to produce a drug eluting balloon.

Example 11

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 0.6 mm upward in the vertical direction (Y-axis direction), and was then moved by 2.0 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 21.8 degrees, with the axis of the balloon as the vertex of the angle.

In addition, the contact length L (theoretical value; see FIG. 39) in contact of the dispensing tube with the balloon outer surface was 3.2 mm.

Example 12

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 1.5 mm upward in the vertical direction (Y-axis direction), and was then moved by 0.9 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 30.0 degrees, with the axis of the balloon as the vertex of the angle.

In addition, the contact length L in contact of the dispensing tube with the outer surface of the balloon was 1.0 mm, and the load exerted on the balloon outer surface due to the contact of the dispensing tube was 1 mN. The load was measured by attaching the dispensing tube to a push-pull gauge, and measuring a reaction force acting on the dispensing tube. Note that the same load measuring method as this was used also in other Examples and Comparative Examples.

Example 13

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 0.4 mm upward in the vertical direction (Y-axis direction), and was then moved by 2.7 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 26.6 degrees, with the axis of the balloon as the vertex of the angle.

In addition, the contact length L in contact of the dispensing tube with the balloon outer surface was 4.0 mm, and the load exerted on the balloon outer surface due to the contact of the dispensing tube was 7 mN.

Example 14

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 1.0 mm upward in the vertical direction (Y-axis direction), and was then moved by 2.0 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 33.7 degrees, with the axis of the balloon as the vertex of the angle.

In addition, the contact length L in contact of the dispensing tube with the balloon outer surface was 2.8 mm.

Example 15

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 1.7 mm upward in the vertical direction (Y-axis direction), and was then moved by 1.4 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 39.0 degrees, with the axis of the balloon as the vertex of the angle.

In addition, the contact length L in contact of the dispensing tube with the balloon outer surface was 1.5 mm, and the load exerted on the balloon outer surface due to the contact of the dispensing tube was 3 mN.

Example 16

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 0.2 mm upward in the vertical direction (Y-axis direction), and was then moved by 0.6 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 3.9 degrees, with the axis of the balloon as the vertex of the angle.

In addition, the contact length L in contact of the dispensing tube with the balloon outer surface was 1.9 mm, and the load exerted on the balloon outer surface due to the contact of the dispensing tube was 7 mN.

Example 17

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 0.2 mm upward in the vertical direction (Y-axis direction), and was then moved by 1.3 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 5.2 degrees, with the axis of the balloon as the vertex of the angle.

In addition, the contact length L in contact of the dispensing tube with the balloon outer surface was 2.8 mm, and the load exerted on the balloon outer surface due to the contact was 15 mN.

Example 18

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 1.2 mm upward in the vertical direction (Y-axis direction), and was then moved by 0.8 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 24.0 degrees, with the axis of the balloon as the vertex of the angle.

In addition, the contact length L in contact of the dispensing tube with the balloon outer surface was 1.2 mm.

Example 19

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 1.1 mm upward in the vertical direction (Y-axis direction), and was then moved by 1.5 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 28.8 degrees, with the axis of the balloon as the vertex of the angle.

In addition, the contact length L in contact of the dispensing tube with the balloon outer surface was 2.2 mm.

Example 20

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 1.1 mm upward in the vertical direction (Y-axis direction), and was then moved by 1.6 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 30.1 degrees, with the axis of the balloon as the vertex of the angle.

In addition, the contact length L in contact of the dispensing tube with the balloon outer surface was 2.3 mm, and the load exerted on the balloon outer surface due to the contact of the dispensing tube was 24 mN.

Example 21

A drug eluting balloon was produced under the same conditions as in Example 10, except for the position of contact of the dispensing tube with the balloon. In bringing the dispensing tube into contact with the balloon, the distal of the dispensing tube was put in contact with the reference position of the outer surface of the balloon in a non-bending manner, was moved from this position by 1.2 mm upward in the vertical direction (Y-axis direction), and was then moved by 1.9 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 36.9 degrees, with the axis of the balloon as the vertex of the angle.

In addition, the contact length L in contact of the dispensing tube with the balloon outer surface was 2.6 mm.

Example 22

(1) Preparation of Coating Solution 14

560 mg of L-serine ethyl ester hydrochloride and 1,344 mg of paclitaxel were weighed. To these compounds were added 11.0 mL of anhydrous ethanol, 16.0 mL of acetone, 4.0 mL of tetrahydrofuran, and 9.0 mL of RO water, to dissolve the compounds, thereby preparing a coating solution 14.

(2) Coating of Balloon with Drug

A balloon catheter (made by Kaneka Corporation; the balloon (expandable portion) was formed from nylon elastomer) measuring 7.0 mm in diameter and 200 mm in length (expandable portion) when expanded was provided. The coating solution 14 was applied to the balloon in an expanded state, in such a manner that the solvent of the coating solution was volatilized slowly and that the amount of paclitaxel in the coating would be approximately 3 μg/mm$^2$.

Specifically, a dispensing tube (outside diameter, 1.50 mm; inside diameter, 1.00 mm; length, 10 mm; the dispensing tube was formed from polyethylene) having an opening portion at a distalmost portion was put in contact with the virtual position of the outer surface of the balloon, and the production was conducted. In bringing the dispensing tube into contact with the balloon, the distal of the dispensing tube was put in contact with the reference position of the outer surface of the balloon in a non-bending manner, and was moved from this position by 0.5 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction by an angle of 0 degrees, with the axis of the balloon as the vertex of the angle. In addition, the length over which the dispensing tube made contact with the balloon outer surface was 1.9 mm, and the load exerted on the balloon outer surface due to the contact of the dispensing tube was 42 mN. Thereafter, while keeping a side surface of the distal of the dispensing tube in contact with the outer surface of the balloon, the drug was discharged from the distal opening portion of the dispensing tube. In this state, the balloon catheter was rotated about the axis of the balloon in the direction opposite (reverse) to the drug discharge direction. By regulating the moving speed of the dispensing tube in the axial direction of the balloon and the rotating speed of the balloon, the drug was discharged, upon the start of rotation, at a rate of 0.7122 μL/second during coating. Thereafter, the thus coated balloon was dried, to produce a drug eluting balloon.

Example 23

A drug eluting balloon was produced under the same conditions as in Example 22, except for the position of contact of the dispensing tube with the balloon. In bringing the dispensing tube into contact with the balloon, the distal of the dispensing tube was put in contact with a reference position of the outer surface of the balloon in a non-bending manner, and was moved from this position by 0.9 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 0 degrees, with the axis of the balloon as the vertex of the angle. In addition, the contact length L in contact of the dispensing tube with the balloon outer surface was 2.5 mm, and the load exerted on the balloon outer surface due to the contact of the dispensing tube was 72 mN.

Example 24

A drug eluting balloon was produced under the same conditions as in Example 22, except for the position of contact of the dispensing tube with the balloon. In bringing the dispensing tube into contact with the balloon, the distal of the dispensing tube was put in contact with a reference position of the outer surface of the balloon in a non-bending manner, and was moved from this position by 1.5 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 0 degrees, with the axis of the balloon as the vertex of the angle. In addition, the contact length L in contact of the dispensing tube with the balloon outer surface was 3.2 mm, and the load exerted on the balloon outer surface due to the contact of the dispensing tube was 117 mN.

Example 25

A drug eluting balloon was produced under the same conditions as in Example 22, except for the position of contact of the dispensing tube with the balloon. In bringing the dispensing tube into contact with the balloon, the distal of the dispensing tube was put in contact with a reference position of the outer surface of the balloon in a non-bending manner, and was moved from this position by 2.4 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 0 degrees, with the axis of the balloon as the vertex of the angle. In addition, the contact length L in contact of the dispensing tube with the balloon outer surface was 4.1 mm, and the load exerted on the balloon outer surface due to the contact of the dispensing tube was 158 mN.

Comparative Example 5

A drug eluting balloon was produced under the same conditions as in Example 10, except for the position of contact of the dispensing tube with the balloon. In bringing the dispensing tube into contact with the balloon, the distal of the dispensing tube was put in contact with a reference position of the outer surface of the balloon in a non-bending manner, was moved from this position by 1.7 mm upward in the vertical direction (Y-axis direction), and was then moved by 2.1 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 50.5 degrees, with the axis of the balloon as the vertex of the angle.

Comparative Example 6

A drug eluting balloon was produced under the same conditions as in Example 10, except for the position of contact of the dispensing tube with the balloon. In bringing the dispensing tube into contact with the balloon, the distal of the dispensing tube was put in contact with a reference position of the outer surface of the balloon in a non-bending manner, was moved from this position by 1.4 mm upward in the vertical direction (Y-axis direction), and was then moved by 2.4 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 51.8 degrees, with the axis of the balloon as the vertex of the angle.

Comparative Example 7

A drug eluting balloon was produced under the same conditions as in Example 10, except for the position of contact of the dispensing tube with the balloon. In bringing the dispensing tube into contact with the balloon, the distal of the dispensing tube was put in contact with a reference position of the outer surface of the balloon in a non-bending manner, was moved from this position by 1.8 mm upward in the vertical direction (Y-axis direction), and was then moved by 1.7 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 45.0 degrees, with the axis of the balloon as the vertex of the angle.

Comparative Example 8

A drug eluting balloon was produced under the same conditions as in Example 10, except for the position of contact of the dispensing tube with the balloon. In bringing the dispensing tube into contact with the balloon, the distal of the dispensing tube was put in contact with a reference position of the outer surface of the balloon in a non-bending manner, was moved from this position by 1.1 mm upward in the vertical direction (Y-axis direction), and was then moved by 2.4 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 45.0 degrees, with the axis of the balloon as the vertex of the angle.

Comparative Example 9

A drug eluting balloon was produced under the same conditions as in Example 22, except for the position of contact of the dispensing tube with the balloon. In bringing the dispensing tube into contact with the balloon, the distal of the dispensing tube was put in contact with a reference position of the outer surface of the balloon in a non-bending manner, and was moved from this position by 3.0 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 0 degrees, with the axis of the balloon as the vertex of the angle. In addition, the contact length L in contact of the dispensing tube with the balloon outer surface was 4.6 mm, and the load exerted on the balloon outer surface due to the contact of the dispensing tube was 182 mN.

Comparative Example 10

A drug eluting balloon was produced under the same conditions as in Example 22, except for the position of contact of the dispensing tube with the balloon. In bringing the dispensing tube into contact with the balloon, the distal of the dispensing tube was put in contact with a reference position of the outer surface of the balloon in a non-bending manner, and was moved from this position by 3.4 mm in a horizontal direction (Z-axis direction), whereby part of a side surface of the distal of the dispensing tube was set along and in contact with the outer surface of the balloon. The virtual position of the distal portion of the dispensing tube in this instance was located at a position deviated from the reference plane toward the balloon rotating direction side by an angle of 0 degrees, with the axis of the balloon as the vertex of the angle. In addition, the contact length L in contact of the dispensing tube with the balloon outer surface was 4.9 mm, and the load exerted on the balloon outer surface due to the contact of the dispensing tube was 190 mN.

Observation of Slip-off of Dispensing Tube

In Examples 10 to 21 and Comparative Examples 5 to 8, it was observed whether or not the dispensing tube slips off from the balloon in such a manner that the discharge direction becomes coincident with the rotating direction of the balloon, from the state where the dispensing tube is in contact with the balloon in such a manner that the discharge direction is opposite to the rotating direction of the balloon, at the time of coating with the drug. In addition, with regard to the drug eluting balloons of Comparative Examples 10 to 15 and Comparative Example 5, the balloon surface was photographed.

In addition, in Examples 22 to 25 and Comparative Examples 9 and 10, it was observed whether or not the dispensing tube slips off from the balloon in such a manner that the discharge direction becomes coincident with the balloon rotating direction, from the state where the dispensing tube is in contact with the balloon in such a manner that the discharge direction is opposite to the balloon rotating direction, at the time of coating with the drug. In addition, with regard to the drug eluting balloons of Examples 22 to 25, the surface was photographed.

Results of Test 3

Table 1 and FIG. 31 show the results of the observation of whether or not the dispensing tube slips off from the balloon, whereas FIGS. 32 to 38 show the pictures of the surfaces of the drug eluting balloons of Examples 10 to 15 and Comparative Example 5.

Figure 40:
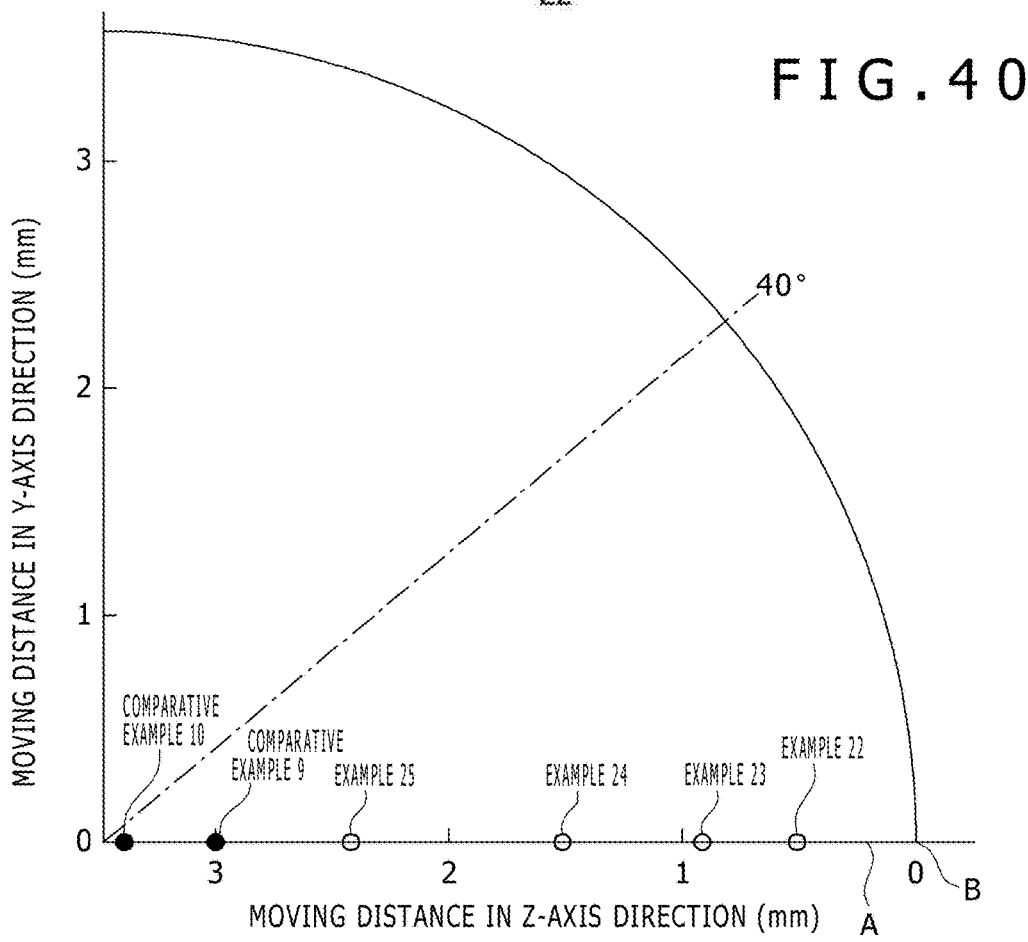
FIG. 40 is a view showing, in terms of coordinates, the positions of contact of a dispensing tube with a balloon, in cases of different dispensing tube diameters.
Figure 41:
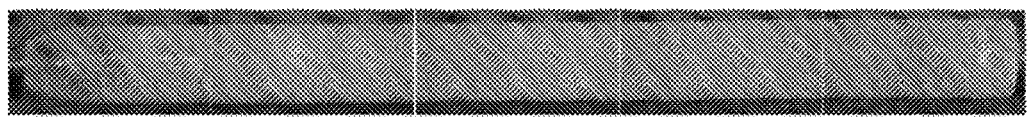
FIG. 41 is a view showing a picture obtained by photographing a surface of a balloon produced in Example 22.
Figure 42:
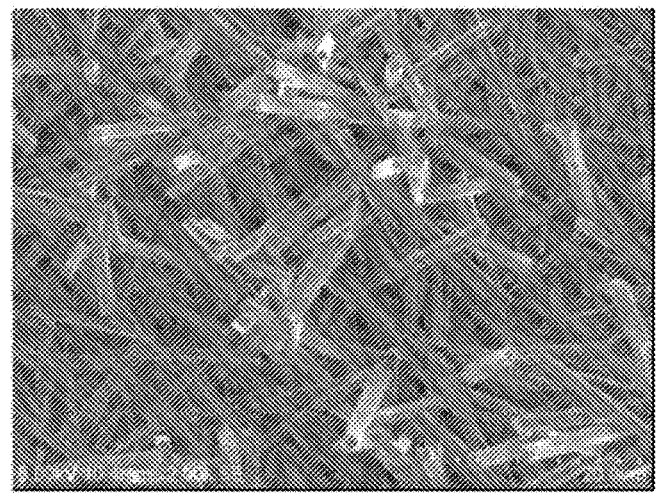
FIG. 42 is a view showing an SEM image (2,000 times) of crystals observed at a substrate surface of a coating layer at a central portion of the balloon shown in FIG.
Figure 43:
FIG. 43 is a view showing a picture obtained by photographing a surface of a balloon produced in Example 23.
Figure 44:
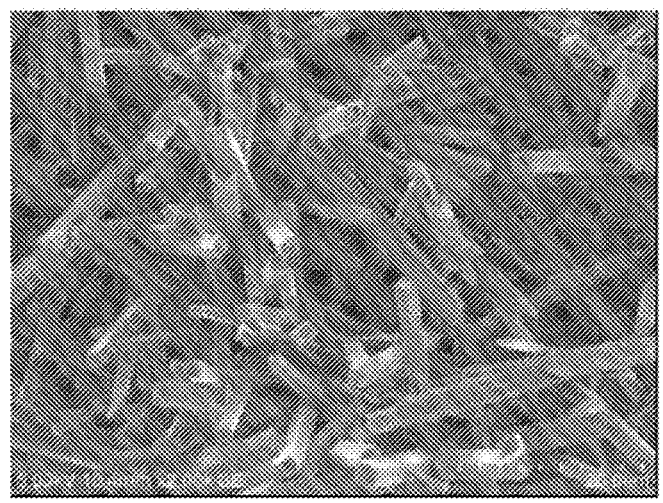
FIG. 44 is a view showing an SEM image (2,000 times) of crystals observed at a substrate surface of a coating layer at a central portion of the balloon shown in FIG. 43.
Figure 45:
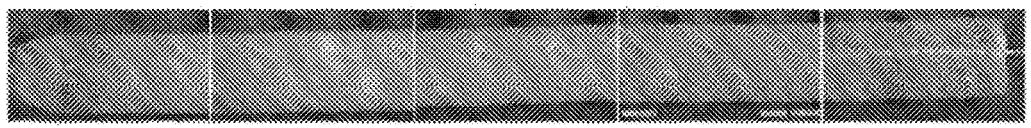
FIG. 45 is a view showing a picture obtained by photographing a surface of a balloon produced in Example 24.
Figure 46:
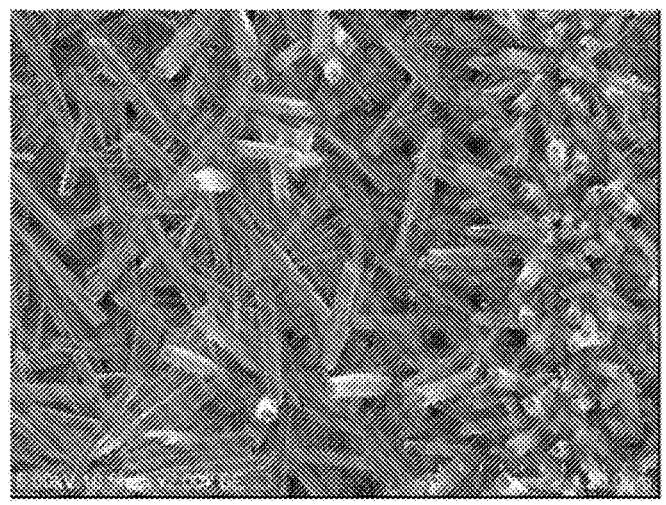
FIG. 46 is a view showing an SEM image (2,000 times) of crystals observed at a substrate surface of a coating layer at a central portion of the balloon shown in FIG. 45.
Figure 47:
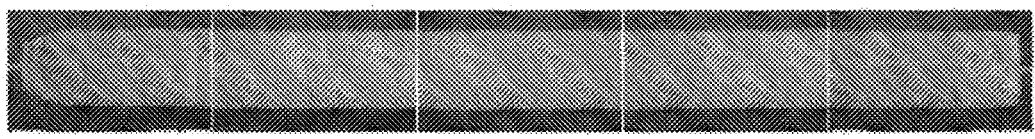
FIG. 47 is a view showing a picture obtained by photographing a surface of a balloon produced in Example 25.
Figure 48:
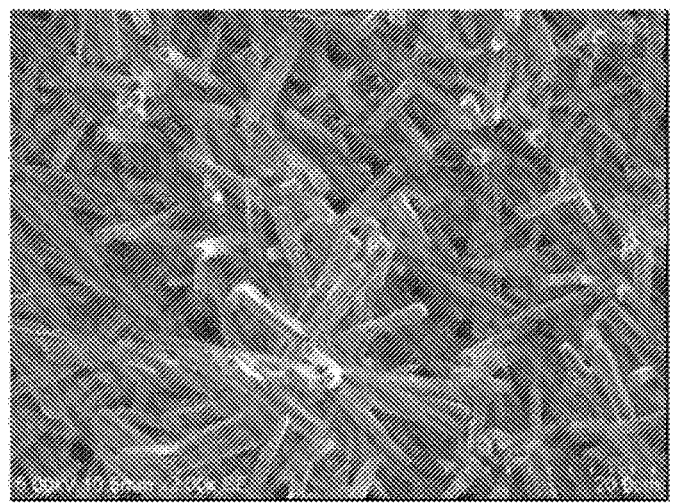
FIG. 48 is a view showing an SEM image (2,000 times) of crystals observed at a substrate surface of a coating layer at a central portion of the balloon shown in FIG. 47.

In addition, Table 2 and FIG. 40 show the results of the observation of whether or not the dispensing tube slips off from the balloon in Examples 22 to 25 and Comparative Examples 9 and 10, and FIGS. 41 to 48 show the pictures of the surfaces of the drug eluting balloons of Examples 22 to 25.

TABLE 1

|  | Moving distance in Y-axis direction (mm) | Moving distance in Z-axis direction (mm) | Angle of virtual position (°) | Load exerted on balloon (mN) | Contact length of tube (mm) | Slip-off of dispensing tube |
|---|---|---|---|---|---|---|
| Example 10 | 0.0 | 0.0 | 0.0 | — | 0.0 | absent |
| Example 11 | 0.6 | 2.0 | 21.8 | — | 3.2 | absent |
| Example 12 | 1.5 | 0.9 | 30.0 | 1 | 1.0 | absent |
| Example 13 | 0.4 | 2.7 | 26.6 | 7 | 4.0 | absent |
| Example 14 | 1.0 | 2.0 | 33.7 | — | 2.8 | absent |
| Example 15 | 1.7 | 1.4 | 39.0 | 3 | 1.5 | absent |
| Example 16 | 0.2 | 0.6 | 3.9 | 7 | 1.9 | absent |
| Example 17 | 0.2 | 1.3 | 5.2 | 15 | 2.8 | absent |
| Example 18 | 1.2 | 0.8 | 24.0 | — | 1.2 | absent |
| Example 19 | 1.1 | 1.5 | 28.8 | — | 2.2 | absent |
| Example 20 | 1.1 | 1.6 | 30.1 | 24 | 2.3 | absent |
| Example 21 | 1.2 | 1.9 | 36.9 | — | 2.6 | absent |
| Comparative Example 5 | 1.7 | 2.1 | 50.5 | — | — | present |
| Comparative Example 6 | 1.4 | 2.4 | 51.8 | — | — | present |
| Comparative Example 7 | 1.8 | 1.7 | 45.0 | — | — | present |
| Comparative Example 8 | 1.1 | 2.4 | 45.0 | — | — | present |

TABLE 2

|  | Moving distance in Y-axis direction (mm) | Moving distance in Z-axis direction (mm) | Angle of virtual position (°) | Load exerted on balloon (mN) | Contact length of tube (mm) | Slip-off of dispensing tube |
|---|---|---|---|---|---|---|
| Example 22 | 0 | 0.5 | 0 | 42 | 1.9 | absent |
| Example 23 | 0 | 0.9 | 0 | 72 | 2.5 | absent |
| Example 24 | 0 | 1.5 | 0 | 117 | 3.2 | absent |
| Example 25 | 0 | 2.4 | 0 | 158 | 4.1 | absent |
| Comparative Example 9 | 0 | 3 | 0 | 182 | 4.6 | present |
| Comparative Example 10 | 0 | 3.4 | 0 | 190 | 4.9 | present |

In Examples 10 to 21 wherein the virtual position of the distal portion of the dispensing tube was located at a position deviated from the reference plane toward the balloon rotating direction side by an angle of 0 degrees to 40 degrees, with the axis of the balloon as the vertex of the angle, it was observed that the position of contact of the dispensing tube with the balloon was maintained favorably, as shown in Table 1 and FIG. 31. In addition, from the pictures of Examples 10 to 15 shown in FIGS. 32 to 37, it was observed that a uniform coating layer free of unevenness of coating was formed over the whole area of the outer surface of the balloon.

Specifically, for example, in Comparative Examples 5 to 8 wherein the virtual position of the distal portion of the dispensing tube was located at a position deviated from the reference plane toward the balloon rotating direction side by an angle of more than 40 degrees, with the axis of the balloon as the vertex of the angle, it was seen from Table 1 and FIG. 31 that the position of contact of the dispensing tube with the balloon was not maintained, that is, the distal portion of the dispensing tube moved, in the course of coating, to such a position that the discharge direction becomes coincident with the rotating direction of the balloon. In Comparative Example 5, the movement of the dispensing tube occurred at the position of P7 shown in FIG. 38, and, at this position, unevenness (non-uniformity) was observed in the coating layer completed.

In Examples 10 to 21 wherein a polyethylene-made dispensing tube having an outside diameter of 0.61 mm and an inside diameter of 0.28 mm was used, it was observed, as shown in Table 1, that the position of contact of the dispensing tube with the balloon is maintained favorably in the case where the contact length of the tube is not more than 4.0 mm. According to Examples 10 to 21, therefore, the contact length of the tube is preferably 0 mm to 4.0 mm, more preferably 1.0 mm to 4.0 mm.

In addition, in Examples 10 to 21, it was observed that the position of contact of the dispensing tube with the balloon is maintained favorably in the case where the load exerted on the balloon is not more than 24 mN. According to Examples 10 to 21, therefore, the load exerted on the balloon is preferably 0 mN to 24 mN, more preferably 1 mN to 24 mN.

Figure 38A:
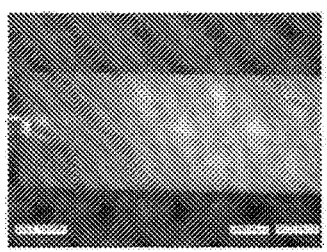
Figure 38B:
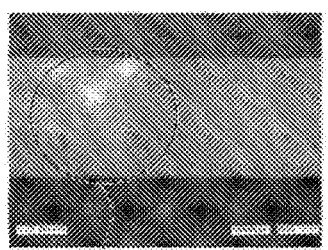
Figure 38C:
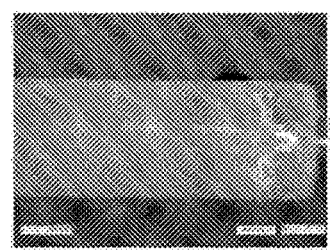

As shown in Table 2 and FIG. 38, in Examples 22 to 25 and Comparative Examples 9 and 10 wherein a polyethylene-made dispensing tube having an outside diameter of 1.50 mm and an inside diameter of 1.00 mm was used, it was observed that the position of contact of the dispensing tube with the balloon is maintained favorably in Examples 22 to 25 wherein the contact length was not more than 4.1 mm. Specifically, for example, in Comparative Examples 9 and 10 wherein the contact length was not less than 4.6 mm, it was observed that the position of contact of the dispensing tube with the balloon is not maintained, and the distal portion of the dispensing tube moved, in the course of coating, to such a position that the discharge direction becomes coincident with the rotating direction of the balloon. According to Examples 22 to 25, therefore, the contact length of the tube is preferably 0 mm to 4.1 mm, more preferably 1.9 mm to 4.1 mm.

In addition, as shown in Table 1, in Examples 22 to 25, it was observed that the position of contact of the dispensing tube with the balloon is maintained favorably in the case where the load exerted on the balloon is not more than 158 mN. According to Examples 22 to 25, therefore, the load exerted on the balloon is preferably 0 mN to 158 mN, more preferably 42 mN to 158 mN.

In addition, from the pictures of Examples 22 to 25 shown in FIGS. 41, 43, 45, and 47, it was observed that a uniform coating layer free of unevenness of coating was formed over the whole area of the outer surface of the balloon. In the coating layers of Examples 22 to 25, a crystal layer of a morphological form including hollow elongate bodies projecting outward in the circumferential direction with respect to the balloon surface was observed, as seen from the SEM pictures shown in FIGS. 42, 44, 46, and 48.

The detailed description above describes a balloon coating method. The invention is not limited, however, to the precise embodiments and variations described. Various changes, modifications and equivalents can effected by one

What is claimed is:

1. A method for forming a coating layer on an outer surface of a balloon of a balloon catheter, the method comprising:
supplying a coating solution containing a drug and a solvent through an end portion of a flexible dispensing tube with an opening portion for discharging the coating solution through the end portion of the flexible dispensing tube;
keeping in contact an opening portion-formed end portion side of the flexible dispensing tube with the outer surface of the balloon in such a manner as to be oriented in a direction opposite to a rotating direction of the balloon;
rotating the balloon about an axis of the balloon; and
discharging the coating solution through the opening portion and applying the coating solution to the outer surface of the balloon while the flexible dispensing tube is moved relative to the balloon in an axial direction of the balloon.

2. The method according to claim 1, comprising:
discharging the coating solution in a state where a continuous length of a side surface on the opening portion-formed end portion side of the flexible dispensing tube is in contact with the outer surface of the balloon.

3. The method according to claim 2, comprising:
discharging the coating solution with the flexible dispensing tube being pressed against the outer surface of the balloon while the flexible dispensing tube is bent.

4. The method according to claim 1, comprising:
discharging the coating solution with the flexible dispensing tube being pressed against the outer surface of the balloon while the flexible dispensing tube is bent.

5. The method according to claim 1, comprising:
discharging the coating solution through the opening portion while the flexible dispensing tube is kept in contact with that portion of the balloon which is rotating toward an upper side in a vertical direction.

6. The method according to claim 1, wherein the drug is rapamycin, paclitaxel, docetaxel, or everolimus.

7. The method according to claim 1, furthe comprising:
moving the flexible dispensing tube, from a state of non-contact with the balloon, in a direction intersecting an extending direction of the flexible dispensing tube, and an opening portion-formed end portion side of the flexible dispensing tube formed at the end portion with the opening portion for discharging the coating solution is thereby placed in contact with the outer surface of the balloon.

8. The method according to claim 1, further comprising:
positioning the flexible dispensing tube relative to the balloon in such a manner that a virtual position at which the opening portion would be located if the flexible dispensing tube is assumed to be non-flexible is located at a position deviated from the reference plane toward the balloon rotating direction side by an angle within the range of 0 degrees to 40 degrees, with the axis of the balloon as the vertex of the angle, in a region extending from the reference plane in a direction opposite to a discharge direction of the flexible dispensing tube.

9. The method according to claim 1, wherein the drug is a water-insoluble drug.

10. A balloon coating method for forming a coating layer on an outer surface of a balloon of a balloon catheter, the balloon coating method comprising:
an application step in which, where a flexible dispensing tube for supplying a coating solution containing a drug and a solvent is formed at an end portion of the flexible dispensig tube with an opening portion for discharging the coating solution through the opening portion and when an opening portion-formed end portion side of the flexible dispensing tube is kept in contact with the outer surface of the balloon in such a manner as to be oriented in a direction opposite to a rotating direction of the balloon while the balloon is rotated about an axis of the balloon, the coating solution is discharged through the opening portion and applied to the outer surface of the balloon while the flexible dispensing tube is moved relative to the balloon in an axial direction of the balloon.

11. A balloon of a balloon catheter, the balloon coated according to the method of claim 1.

12. A balloon of a balloon catheter, the balloon coated according to the balloon coating method of claim 10.

13. The balloon coating method according to claim 10, wherein in the application step, the coating solution is discharged, with the flexible dispensing tube being pressed against the outer surface of the balloon while the flexible dispensing tube is bent.

14. The balloon coating method according to claim 10, wherein in the application step, the coating solution is discharged in a state where a continuous length of a side surface on the opening portion-formed end portion side of the flexible dispensing tube is in contact with the outer surface of the balloon.

15. The balloon coating method according to claim 14, wherein in the application step, the coating solution is discharged, with the flexible dispensing tube being pressed against the outer surface of the balloon while the flexible dispensing tube is bent.

16. The balloon coating method according to claim 10, wherein in the application step, the coating solution is discharged through the opening portion while the flexible dispensing tube is kept in contact with that portion of the balloon which is rotating toward an upper side in a vertical direction.

17. The balloon coating method according to claim 10, wherein the drug is rapamycin, paclitaxel, docetaxel, or everolimus.

18. The balloon coating method according to claim 10, further comprising:
a positioning step in which the flexible dispensing tube is moved, from a state of non-contact with the balloon, in a direction intersecting an extending direction of the flexible dispensing tube, and an opening portion-formed end portion side of the flexible dispensing tube formed at the end portion with the opening portion for discharging the coating solution is thereby placed in contact with the outer surface of the balloon.

19. The ballon coating method according to claim 10, further comprising:
a positioning step in which the flexible dispensing tube is positioned relative to the balloon in such a manner that a virtual position at which the opening portion would be located if the flexible dispensing tube is assumed to be non-flexible is located at a position deviated from the reference plane toward the balloon rotating direction side by an angle within the range of 0 degrees to 40 degrees, with the axis of the balloon as the vertex of the angle, in a region extending from the reference plane in a direction opposite to a discharge direction of the flexible dispensing tube.

20. The ballon coating method according to claim 10, wherein the drug is a water-insoluble drug.

* * * * *